United States Patent [19]

Glimcher et al.

[11] Patent Number: 5,672,473

[45] Date of Patent: Sep. 30, 1997

[54] METHODS OF IDENTIFYING COMPOUNDS USEFUL FOR TREATING AUTOIMMUNE DISEASES

[75] Inventors: Laurie H. Glimcher, W. Newton; Hong Zhou, Watertown; John Douhan, III, Boston, all of Mass.

[73] Assignee: President and Fellows of Harvard College, Cambridge, Mass.

[21] Appl. No.: 295,502

[22] Filed: Aug. 24, 1994

[51] Int. Cl.$^6$ .................. C07H 21/00; C07K 14/705; C12Q 1/68; G01N 33/566

[52] U.S. Cl. .............. 435/6; 435/7.24; 435/7.8; 435/29; 435/172.3; 436/501; 530/358; 536/23.5

[58] Field of Search ............... 435/7.24, 7.8, 435/29, 172.3, 6; 436/501; 530/358; 536/23.5

[56] References Cited

FOREIGN PATENT DOCUMENTS 0648836  4/1995  European Pat. Off. .

OTHER PUBLICATIONS

Begovich A.B. et al.; "A Specific HLA–DPβ Allele is Associated With Pauciarticular Juvenile Rheumatoid Arthritis But Not Adult Rheumatoid Arthritis"; *Proc. Natl. Acad. Sci. USA* 86:9489–9493 (1989).

Gyuris J. et al.; "Cdi1, A Human G1 and S Phase Protein Phosphatase That Associates With Cdk2"; *Cell* 75:791–803 (1993).

Keegan L. et al.; "Separation of DNA Binding from the Transcription–Activating Function of a Eukaryotic Regulatory Protein"; *Science* 231:699–703 (1986).

Lin Y. et al.; "GAL4 Derivatives Function Alone and Synergistically with Mammalian Activators In Vitro"; *Cell* 54:659–664 (1988).

Lin Y. et al.; "Mechanism of Action of Acidic Transcriptional Activator In Vitro"; *Cell* 64:971–981 (1991).

Ma J. et al.; "Converting a Eukaryotic Transcriptional Inhibitor into an Activator"; *Cell* 55:443–446 (1988).

Ma J. et al.; "Deletion Analysis of GAL4 Defines Two Transcriptional Activating Segments"; *Cell* 48:847–853 (1987).

McDermott M. et al.; "The Immunogenetics of Rheumatic Diseases"; *Bulletin on the Rheumatic Diseases* 38:1–10 (1988).

Ono S.J. et al.; "An Isotype–Specific Trans–Acting Factor Is Defective in a Mutant B Cell Line That Expresses HLA–DQ But Not –DR or –DP"; *J. Exp. Med.* 173:629–637 (1991).

Roberts S.G.E. et al.; "Interaction Between an Acidic Activator and Transcription Factor TFIIB is Required for Transcriptional Activation"; *Nature* 363:741–744 (1993).

Sadowski I. et al.; "GAL4–VP16 is an Unusually Potent Transcriptional Activator"; *Nature* 335:563–564 (1988).

Scharf S.J. et al.; "Specific HLA–DQB and HLA–DRB1 Alleles Confer Susceptibility to Pemphigus Vulgaris"; *Proc. Natl. Acad. Sci. USA* 86:6215–6219 (1989).

Steimle V. et al.; "Complementation Cloning of an MHC Class II Transactivator Mutated in Hereditary MHC Class II Deficiency (or Bare Lymphocyte Syndrome)"; *Cell* 75:135–146 (1993).

Zervos A.S. et al., "Mxi1, A Protein That Specifically Interacts with Max to Bind Myc–Max Recognition Sites"; *Cell* 72:223–232 (1993).

R. Lewin, *Science*, 237, 1570 (1987).

*Primary Examiner*—David Saunders
*Attorney, Agent, or Firm*—Fish & Richardson P.C.

[57] ABSTRACT

Disclosed are methods of identifying compounds which inhibit transcription activation by CIITA and thus inhibit MHC class II gene expression. Such compounds can affect the induction of an immune response. The methods employ, independently, the activation and interactions domains of CIITA. The methods also employ the activation and interaction domains of isotype-specific CIITA proteins, allowing for the identification of compounds which are isotype-specific inhibitors of transcription and which are useful for selectively affecting the immune system.

25 Claims, 17 Drawing Sheets

```
ATG CGT TGC CTG GCT CCA CGC CCT GCT GGG TCC TAC CTG TCA GAG CCC              48
Met Arg Cys Leu Ala Pro Arg Pro Ala Gly Ser Tyr Leu Ser Glu Pro
 1               5                   10                  15

CAA GGC AGC TCA CAG TGT GCC ACC ATG GAG TTG GGG CCC CTA GAA GGT              96
Gln Gly Ser Ser Gln Cys Ala Thr Met Glu Leu Gly Pro Leu Glu Gly
                20                  25                  30

GGC TAC CTG GAG CTT CTT AAC AGC GAT GCT GAC CCC CTG TGC CTC TAC             144
Gly Tyr Leu Glu Leu Leu Asn Ser Asp Ala Asp Pro Leu Cys Leu Tyr
        35                  40                  45

CAC TTC TAT GAC CAG ATG GAC CTG GCT GGA GAA GAA GAG ATT GAG CTC             192
His Phe Tyr Asp Gln Met Asp Leu Ala Gly Glu Glu Glu Ile Glu Leu
        50                  55                  60

TAC TCA GAA CCC GAC ACA GAC ACC ATC AAC TGC GAC CAG TTC AGC AGG             240
Tyr Ser Glu Pro Asp Thr Asp Thr Ile Asn Cys Asp Gln Phe Ser Arg
65                  70                  75                  80

CTG TTG TGT GAC ATG GAA GGT GAT GAA GAG ACC AGG GAG GCT TAT GCC             288
Leu Leu Cys Asp Met Glu Gly Asp Glu Glu Thr Arg Glu Ala Tyr Ala
                85                  90                  95

AAT ATC GCG GAA CTG GAC CAG TAT GTC TTC CAG GAC TCC CAG CTG GAG             336
Asn Ile Ala Glu Leu Asp Gln Tyr Val Phe Gln Asp Ser Gln Leu Glu
                100                 105                 110

GGC CTG AGC AAG GAC ATT TTC AAG CAC ATA GGA CCA GAT GAA GTG ATC             384
Gly Leu Ser Lys Asp Ile Phe Lys His Ile Gly Pro Asp Glu Val Ile
            115                 120                 125

GGT GAG AGT ATG GAG ATG CCA GCA GAA GTT GGG CAG AAA AGT CAG AAA             432
Gly Glu Ser Met Glu Met Pro Ala Glu Val Gly Gln Lys Ser Gln Lys
130                 135                 140

AGA CCC TTC CCA GAG GAG CTT CCG GCA GAC CTG AAG CAC TGG AAG CCA             480
Arg Pro Phe Pro Glu Glu Leu Pro Ala Asp Leu Lys His Trp Lys Pro
145                 150                 155                 160

GCT GAG CCC CCC ACT GTG GTG ACT GGC AGT CTC CTA GTG GGA CCA GTG             528
Ala Glu Pro Pro Thr Val Val Thr Gly Ser Leu Leu Val Gly Pro Val
                165                 170                 175

AGC GAC TGC TCC ACC CTG CCC TGC CTG CCA CTG CCT GCG CTG TTC AAC             576
Ser Asp Cys Ser Thr Leu Pro Cys Leu Pro Leu Pro Ala Leu Phe Asn
            180                 185                 190

CAG GAG CCA GCC TCC GGC CAG ATG CGC CTG GAG AAA ACC GAC CAG ATT             624
Gln Glu Pro Ala Ser Gly Gln Met Arg Leu Glu Lys Thr Asp Gln Ile
            195                 200                 205

CCC ATG CCT TTC TCC AGT TCC TCG TTG AGC TGC CTG AAT CTC CCT GAG             672
Pro Met Pro Phe Ser Ser Ser Ser Leu Ser Cys Leu Asn Leu Pro Glu
210                 215                 220

GGA CCC ATC CAG TTT GTC CCC ACC ATC TCC ACT CTG CCC CAT GGG CTC             720
Gly Pro Ile Gln Phe Val Pro Thr Ile Ser Thr Leu Pro His Gly Leu
225                 230                 235                 240

TGG CAA ATC TCT GAG GCT GGA ACA GGG GTC TCC AGT ATA TTC ATC TAC             768
Trp Gln Ile Ser Glu Ala Gly Thr Gly Val Ser Ser Ile Phe Ile Tyr
                245                 250                 255

CAT GGT GAG GTG CCC CAG GCC AGC CAA GTA CCC CCT CCC AGT GGA TTC             816
His Gly Glu Val Pro Gln Ala Ser Gln Val Pro Pro Pro Ser Gly Phe
            260                 265                 270
```

FIG. 1A

```
ACT GTC CAC GGC CTC CCA ACA TCT CCA GAC CGG CCA GGC TCC ACC AGC      864
Thr Val His Gly Leu Pro Thr Ser Pro Asp Arg Pro Gly Ser Thr Ser
        275                 280                 285

CCC TTC GCT CCA TCA GCC ACT GAC CTG CCC AGC ATG CCT GAA CCT GCC      912
Pro Phe Ala Pro Ser Ala Thr Asp Leu Pro Ser Met Pro Glu Pro Ala
        290                 295                 300

CTG ACC TCC CGA GCA AAC ATG ACA GAG CAC AAG ACG TCC CCC ACC CAA      960
Leu Thr Ser Arg Ala Asn Met Thr Glu His Lys Thr Ser Pro Thr Gln
305                 310                 315                 320

TGC CCG GCA GCT GGA GAG GTC TCC AAC AAG CTT CCA AAA TGG CCT GAG     1008
Cys Pro Ala Ala Gly Glu Val Ser Asn Lys Leu Pro Lys Trp Pro Glu
                325                 330                 335

CCG GTG GAG CAG TTC TAC CGC TCA CTG CAG GAC ACG TAT GGT GCC GAG     1056
Pro Val Glu Gln Phe Tyr Arg Ser Leu Gln Asp Thr Tyr Gly Ala Glu
        340                 345                 350

CCC GCA GGC CCG GAT GGC ATC CTA GTG GAG GTG GAT CTG GTG CAG GCC     1104
Pro Ala Gly Pro Asp Gly Ile Leu Val Glu Val Asp Leu Val Gln Ala
        355                 360                 365

AGG CTG GAG AGG AGC AGC AGC AAG AGC CTG GAG CGG GAA CTG GCC ACC     1152
Arg Leu Glu Arg Ser Ser Ser Lys Ser Leu Glu Arg Glu Leu Ala Thr
        370                 375                 380

CCG GAC TGG GCA GAA CGG CAG CTG GCC CAA GGA GGC CTG GCT GAG GTG     1200
Pro Asp Trp Ala Glu Arg Gln Leu Ala Gln Gly Gly Leu Ala Glu Val
385                 390                 395                 400

CTG TTG GCT GCC AAG GAG CAC CGG CGG CCG CGT GAG ACA CGA GTG ATT     1248
Leu Leu Ala Ala Lys Glu His Arg Arg Pro Arg Glu Thr Arg Val Ile
                405                 410                 415

GCT GTG CTG GGC AAA GCT GGT CAG GGC AAG AGC TAT TGG GCT GGG GCA     1296
Ala Val Leu Gly Lys Ala Gly Gln Gly Lys Ser Tyr Trp Ala Gly Ala
        420                 425                 430

GTG AGC CGG GCC TGG GCT TGT GGC CGG CTT CCC CAG TAC GAC TTT GTC     1344
Val Ser Arg Ala Trp Ala Cys Gly Arg Leu Pro Gln Tyr Asp Phe Val
        435                 440                 445

TTC TCT GTC CCC TGC CAT TGC TTG AAC CGT CCG GGG GAT GCC TAT GGC     1392
Phe Ser Val Pro Cys His Cys Leu Asn Arg Pro Gly Asp Ala Tyr Gly
450                 455                 460

CTG CAG GAT CTG CTC TTC TCC CTG GGC CCA CAG CCA CTC GTG GCG GCC     1440
Leu Gln Asp Leu Leu Phe Ser Leu Gly Pro Gln Pro Leu Val Ala Ala
465                 470                 475                 480

GAT GAG GTT TTC AGC CAC ATC TTG AAG AGA CCT GAC CGC GTT CTG CTC     1488
Asp Glu Val Phe Ser His Ile Leu Lys Arg Pro Asp Arg Val Leu Leu
                485                 490                 495

ATC CTA GAC GCC TTC GAG GAG CTG GAA GCG CAA GAT GGC TTC CTG CAC     1536
Ile Leu Asp Ala Phe Glu Glu Leu Glu Ala Gln Asp Gly Phe Leu His
        500                 505                 510

AGC ACG TGC GGA CCG GCA CCG GCG GAG CCC TGC TCC CTC CGG GGG CTG     1584
Ser Thr Cys Gly Pro Ala Pro Ala Glu Pro Cys Ser Leu Arg Gly Leu
        515                 520                 525
```

FIG. 1B

```
CTG GCC GGC CTT TTC CAG AAG AAG CTG CTC CGA GGT TGC ACC CTC CTC    1632
Leu Ala Gly Leu Phe Gln Lys Lys Leu Leu Arg Gly Cys Thr Leu Leu
        530                 535                 540

CTC ACA GCC CGG CCC CGG GGC CGC CTG GTC CAG AGC CTG AGC AAG GCC    1680
Leu Thr Ala Arg Pro Arg Gly Arg Leu Val Gln Ser Leu Ser Lys Ala
545                 550                 555                 560

GAC GCC CTA TTT GAG CTG TCC GGC TTC TCC ATG GAG CAG GCC CAG GCA    1728
Asp Ala Leu Phe Glu Leu Ser Gly Phe Ser Met Glu Gln Ala Gln Ala
                565                 570                 575

TAC GTG ATG CGC TAC TTT GAG AGC TCA GGG ATG ACA GAG CAC CAA GAC    1776
Tyr Val Met Arg Tyr Phe Glu Ser Ser Gly Met Thr Glu His Gln Asp
        580                 585                 590

AGA GCC CTG ACG CTC CTC CGG GAC CGG CCA CTT CTT CTC AGT CAC AGC    1824
Arg Ala Leu Thr Leu Leu Arg Asp Arg Pro Leu Leu Leu Ser His Ser
        595                 600                 605

CAC AGC CCT ACT TTG TGC CGG GCA GTG TGC CAG CTC TCA GAG GCC CTG    1872
His Ser Pro Thr Leu Cys Arg Ala Val Cys Gln Leu Ser Glu Ala Leu
        610                 615                 620

CTG GAG CTT GGG GAG GAC GCC AAG CTG CCC TCC ACG CTC ACG GGA CTC    1920
Leu Glu Leu Gly Glu Asp Ala Lys Leu Pro Ser Thr Leu Thr Gly Leu
625                 630                 635                 640

TAT GTC GGC CTG CTG GGC CGT GCA GCC CTC GAC AGC CCC CCC GGG GCC    1968
Tyr Val Gly Leu Leu Gly Arg Ala Ala Leu Asp Ser Pro Pro Gly Ala
                645                 650                 655

CTG GCA GAG CTG GCC AAG CTG GCC TGG GAG CTG GGC CGC AGA CAT CAA    2016
Leu Ala Glu Leu Ala Lys Leu Ala Trp Glu Leu Gly Arg Arg His Gln
        660                 665                 670

AGT ACC CTA CAG GAG GAC CAG TTC CCA TCC GCA GAC GTG AGG ACC TGG    2064
Ser Thr Leu Gln Glu Asp Gln Phe Pro Ser Ala Asp Val Arg Thr Trp
        675                 680                 685

GCG ATG GCC AAA GGC TTA GTC CAA CAC CCA CCG CGG GCC GCA GAG TCC    2112
Ala Met Ala Lys Gly Leu Val Gln His Pro Pro Arg Ala Ala Glu Ser
690                 695                 700

GAG CTG GCC TTC CCC AGC TTC CTC CTG CAA TGC TTC CTG GGG GCC CTG    2160
Glu Leu Ala Phe Pro Ser Phe Leu Leu Gln Cys Phe Leu Gly Ala Leu
705                 710                 715                 720

TGG CTG GCT CTG AGT GGC GAA ATC AAG GAC AAG GAG CTC CCG CAG TAC    2208
Trp Leu Ala Leu Ser Gly Glu Ile Lys Asp Lys Glu Leu Pro Gln Tyr
                725                 730                 735

CTA GCA TTG ACC CCA AGG AAG AAG AGG CCC TAT GAC AAC TGG CTG GAG    2256
Leu Ala Leu Thr Pro Arg Lys Lys Arg Pro Tyr Asp Asn Trp Leu Glu
        740                 745                 750

GGC GTG CCA CGC TTT CTG GCT GGG CTG ATC TTC CAG CCT CCC GCC CGC    2304
Gly Val Pro Arg Phe Leu Ala Gly Leu Ile Phe Gln Pro Pro Ala Arg
        755                 760                 765

TGC CTG GGA GCC CTA CTC GGG CCA TCG GCG GCT GCC TCG GTG GAC AGG    2352
Cys Leu Gly Ala Leu Leu Gly Pro Ser Ala Ala Ala Ser Val Asp Arg
770                 775                 780
```

FIG. 1C

```
AAG CAG AAG GTG CTT GCG AGG TAC CTG AAG CGG CTG CAG CCG GGG ACA       2400
Lys Gln Lys Val Leu Ala Arg Tyr Leu Lys Arg Leu Gln Pro Gly Thr
785             790             795             800

CTG CGG GCG CGG CAG CTG CTT GAG CTG CTC CAC TGC GCC CAC GAG GCC       2448
Leu Arg Ala Arg Gln Leu Leu Glu Leu Leu His Cys Ala His Glu Ala
                805             810             815

GAG GAG GCT GGA ATT TGG CAG CAC GTG GTA CAG GAG CTC CCC GGC CGC       2496
Glu Glu Ala Gly Ile Trp Gln His Val Val Gln Glu Leu Pro Gly Arg
            820             825             830

CTC TCT TTT CTG GGC ACC CGC CTC ACG CCT CCT GAT GCA CAT GTA CTG       2544
Leu Ser Phe Leu Gly Thr Arg Leu Thr Pro Pro Asp Ala His Val Leu
        835             840             845

GGC AAG GCC TTG GAG GCG GCG GGC CAA GAC TTC TCC CTG GAC CTC CGC       2592
Gly Lys Ala Leu Glu Ala Ala Gly Gln Asp Phe Ser Leu Asp Leu Arg
850             855             860

AGC ACT GGC ATT TGC CCC TCT GGA TTG GGG AGC CTC GTG GGA CTC AGC       2640
Ser Thr Gly Ile Cys Pro Ser Gly Leu Gly Ser Leu Val Gly Leu Ser
865             870             875             880

TGT GTC ACC CGT TTC AGG GCT GCC TTG AGC GAC ACG GTG GCG CTG TGG       2688
Cys Val Thr Arg Phe Arg Ala Ala Leu Ser Asp Thr Val Ala Leu Trp
            885             890             895

GAG TCC CTG CGG CAG CAT GGG GAG ACC AAG CTA CTT CAG GCA GCA GAG       2736
Glu Ser Leu Arg Gln His Gly Glu Thr Lys Leu Leu Gln Ala Ala Glu
        900             905             910

GAG AAG TTC ACC ATC GAG CCT TTC AAA GCC AAG TCC CTG AAG GAT GTG       2784
Glu Lys Phe Thr Ile Glu Pro Phe Lys Ala Lys Ser Leu Lys Asp Val
        915             920             925

GAA GAC CTG GGA AAG CTT GTG CAG ACT CAG AGG ACG AGA AGT TCC TCG       2832
Glu Asp Leu Gly Lys Leu Val Gln Thr Gln Arg Thr Arg Ser Ser Ser
930             935             940

GAA GAC ACA GCT GGG GAG CTC CCT GCT GTT CGG GAC CTA AAG AAA CTG       2880
Glu Asp Thr Ala Gly Glu Leu Pro Ala Val Arg Asp Leu Lys Lys Leu
945             950             955             960

GAG TTT GCG CTG GGC CCT GTC TCA GGC CCC CAG GCT TTC CCC AAA CTG       2928
Glu Phe Ala Leu Gly Pro Val Ser Gly Pro Gln Ala Phe Pro Lys Leu
            965             970             975

GTG CGG ATC CTC ACG GCC TTT TCC TCC CTG CAG CAT CTG GAC CTG GAT       2976
Val Arg Ile Leu Thr Ala Phe Ser Ser Leu Gln His Leu Asp Leu Asp
        980             985             990

GCG CTG AGT GAG AAC AAG ATC GGG GAC GAG GGT GTC TCG CAG CTC TCA       3024
Ala Leu Ser Glu Asn Lys Ile Gly Asp Glu Gly Val Ser Gln Leu Ser
        995             1000            1005

GCC ACC TTC CCC CAG CTG AAG TCC TTG GAA ACC CTC AAT CTG TCC CAG       3072
Ala Thr Phe Pro Gln Leu Lys Ser Leu Glu Thr Leu Asn Leu Ser Gln
1010            1015            1020

AAC AAC ATC ACT GAC CTG GGT GCC TAC AAA CTC GCC GAG GCC CTG CCT       3120
Asn Asn Ile Thr Asp Leu Gly Ala Tyr Lys Leu Ala Glu Ala Leu Pro
1025            1030            1035            1040
```

FIG. 1D

```
TCG CTC GCT GCA TCC CTG CTC AGG CTA AGC TTG TAC AAT AAC TGC ATC        3168
Ser Leu Ala Ala Ser Leu Leu Arg Leu Ser Leu Tyr Asn Asn Cys Ile
            1045                1050                1055

TGC GAC GTG GGA GCC GAG AGC TTG GCT CGT GTG CTT CCG GAC ATG GTG        3216
Cys Asp Val Gly Ala Glu Ser Leu Ala Arg Val Leu Pro Asp Met Val
            1060                1065                1070

TCC CTC CGG GTG ATG GAC GTC CAG TAC AAC AAG TTC ACG GCT GCC GGG        3264
Ser Leu Arg Val Met Asp Val Gln Tyr Asn Lys Phe Thr Ala Ala Gly
        1075                1080                1085

GCC CAG CAG CTC GCT GCC AGC CTT CGG AGG TGT CCT CAT GTG GAG ACG        3312
Ala Gln Gln Leu Ala Ala Ser Leu Arg Arg Cys Pro His Val Glu Thr
        1090                1095                1100

CTG GCG ATG TGG ACG CCC ACC ATC CCA TTC AGT GTC CAG GAA CAC CTG        3360
Leu Ala Met Trp Thr Pro Thr Ile Pro Phe Ser Val Gln Glu His Leu
1105                1110                1115                1120

CAA CAA CAG GAT TCA CGG ATC AGC CTG AGA TGA                            3393
Gln Gln Gln Asp Ser Arg Ile Ser Leu Arg  *
                1125                1130
```

FIG. 1E

Determination of the Molecular Biological Function of CIITA

Assay system: The full length CIITA, its 5' and 3' deletion mutants were fused to LexA (an *E. coli* repressor protein) N-Terminal 202 a.a. dimerization/DNA binding domain, transfected to a yeast transformant bearing a reporter plasmid, pSH34-18, and plated on X-gal containing medium.

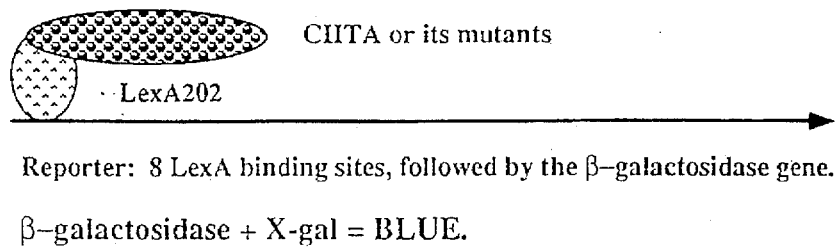

Reporter: 8 LexA binding sites, followed by the β-galactosidase gene.

β-galactosidase + X-gal = BLUE.

| CIITA test constructs | | Transcription activity (blue/white test) |
|---|---|---|
| pEG.CIITA | | Blue |
| pEG.ciita.N70 | | Blue |
| pEG.ciiTA.N56 | | Blue |
| pEG.ciita.N29 | | Blue |
| pEG.CIITA.C14 | | White |
| pEG.CIITA.C30 | | White |
| pEG.CIITA.C50 | | White |
| pEG.CIITA.C74 | | White |
| pEG.ciita.N22 | (Only with domain I, II, and III, no IV) | Blue |
| pEG.ciita.N17 | (Only with domain I and II) | Blue |
| pEG.ciita.N12.8 | (Only with domain I, the acidic domain) | Blue |
| pEG.ciita.N7.6 | (Only with partial domain I) | Blue |

FIG. 2

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 3393 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..3393

( x i ) SEQUENCE DESCRIPTION: SEQ ID NO:1:

```
ATG  CGT  TGC  CTG  GCT  CCA  CGC  CCT  GCT  GGG  TCC  TAC  CTG  TCA  GAG  CCC         48
Met  Arg  Cys  Leu  Ala  Pro  Arg  Pro  Ala  Gly  Ser  Tyr  Leu  Ser  Glu  Pro
 1              5                        10                       15

CAA  GGC  AGC  TCA  CAG  TGT  GCC  ACC  ATG  GAG  TTG  GGG  CCC  CTA  GAA  GGT         96
```

|  |  |  |  |  |  |  |  |  |  |  |  |  |  |  |  |
|---|---|---|---|---|---|---|---|---|---|---|---|---|---|---|---|
| Gln | Gly | Ser | Ser<br>20 | Gln | Cys | Ala | Thr | Met<br>25 | Glu | Leu | Gly | Pro | Leu<br>30 | Glu | Gly |

| GGC | TAC | CTG | GAG | CTT | CTT | AAC | AGC | GAT | GCT | GAC | CCC | CTG | TGC | CTC | TAC | 144 |
|---|---|---|---|---|---|---|---|---|---|---|---|---|---|---|---|---|
| Gly | Tyr | Leu<br>35 | Glu | Leu | Leu | Asn | Ser<br>40 | Asp | Ala | Asp | Pro | Leu<br>45 | Cys | Leu | Tyr | |

| CAC | TTC | TAT | GAC | CAG | ATG | GAC | CTG | GCT | GGA | GAA | GAA | GAG | ATT | GAG | CTC | 192 |
|---|---|---|---|---|---|---|---|---|---|---|---|---|---|---|---|---|
| His | Phe<br>50 | Tyr | Asp | Gln | Met | Asp<br>55 | Leu | Ala | Gly | Glu | Glu<br>60 | Glu | Ile | Glu | Leu | |

| TAC | TCA | GAA | CCC | GAC | ACA | GAC | ACC | ATC | AAC | TGC | GAC | CAG | TTC | AGC | AGG | 240 |
|---|---|---|---|---|---|---|---|---|---|---|---|---|---|---|---|---|
| Tyr<br>65 | Ser | Glu | Pro | Asp | Thr<br>70 | Asp | Thr | Ile | Asn | Cys<br>75 | Asp | Gln | Phe | Ser | Arg<br>80 | |

| CTG | TTG | TGT | GAC | ATG | GAA | GGT | GAT | GAA | GAG | ACC | AGG | GAG | GCT | TAT | GCC | 288 |
|---|---|---|---|---|---|---|---|---|---|---|---|---|---|---|---|---|
| Leu | Leu | Cys | Asp | Met<br>85 | Glu | Gly | Asp | Glu | Glu<br>90 | Thr | Arg | Glu | Ala | Tyr<br>95 | Ala | |

| AAT | ATC | GCG | GAA | CTG | GAC | CAG | TAT | GTC | TTC | CAG | GAC | TCC | CAG | CTG | GAG | 336 |
|---|---|---|---|---|---|---|---|---|---|---|---|---|---|---|---|---|
| Asn | Ile | Ala | Glu<br>100 | Leu | Asp | Gln | Tyr | Val<br>105 | Phe | Gln | Asp | Ser | Gln<br>110 | Leu | Glu | |

| GGC | CTG | AGC | AAG | GAC | ATT | TTC | AAG | CAC | ATA | GGA | CCA | GAT | GAA | GTG | ATC | 384 |
|---|---|---|---|---|---|---|---|---|---|---|---|---|---|---|---|---|
| Gly | Leu | Ser<br>115 | Lys | Asp | Ile | Phe | Lys<br>120 | His | Ile | Gly | Pro | Asp<br>125 | Glu | Val | Ile | |

| GGT | GAG | AGT | ATG | GAG | ATG | CCA | GCA | GAA | GTT | GGG | CAG | AAA | AGT | CAG | AAA | 432 |
|---|---|---|---|---|---|---|---|---|---|---|---|---|---|---|---|---|
| Gly<br>130 | Glu | Ser | Met | Glu | Met<br>135 | Pro | Ala | Glu | Val | Gly<br>140 | Gln | Lys | Ser | Gln | Lys | |

| AGA | CCC | TTC | CCA | GAG | GAG | CTT | CCG | GCA | GAC | CTG | AAG | CAC | TGG | AAG | CCA | 480 |
|---|---|---|---|---|---|---|---|---|---|---|---|---|---|---|---|---|
| Arg<br>145 | Pro | Phe | Pro | Glu | Glu<br>150 | Leu | Pro | Ala | Asp | Leu<br>155 | Lys | His | Trp | Lys | Pro<br>160 | |

| GCT | GAG | CCC | CCC | ACT | GTG | GTG | ACT | GGC | AGT | CTC | CTA | GTG | GGA | CCA | GTG | 528 |
|---|---|---|---|---|---|---|---|---|---|---|---|---|---|---|---|---|
| Ala | Glu | Pro | Pro | Thr<br>165 | Val | Val | Thr | Gly | Ser<br>170 | Leu | Leu | Val | Gly | Pro<br>175 | Val | |

| AGC | GAC | TGC | TCC | ACC | CTG | CCC | TGC | CTG | CCA | CTG | CCT | GCG | CTG | TTC | AAC | 576 |
|---|---|---|---|---|---|---|---|---|---|---|---|---|---|---|---|---|
| Ser | Asp | Cys | Ser<br>180 | Thr | Leu | Pro | Cys | Leu<br>185 | Pro | Leu | Pro | Ala | Leu<br>190 | Phe | Asn | |

| CAG | GAG | CCA | GCC | TCC | GGC | CAG | ATG | CGC | CTG | GAG | AAA | ACC | GAC | CAG | ATT | 624 |
|---|---|---|---|---|---|---|---|---|---|---|---|---|---|---|---|---|
| Gln | Glu | Pro<br>195 | Ala | Ser | Gly | Gln | Met<br>200 | Arg | Leu | Glu | Lys | Thr<br>205 | Asp | Gln | Ile | |

| CCC | ATG | CCT | TTC | TCC | AGT | TCC | TCG | TTG | AGC | TGC | CTG | AAT | CTC | CCT | GAG | 672 |
|---|---|---|---|---|---|---|---|---|---|---|---|---|---|---|---|---|
| Pro | Met<br>210 | Pro | Phe | Ser | Ser | Ser<br>215 | Ser | Leu | Ser | Cys | Leu<br>220 | Asn | Leu | Pro | Glu | |

| GGA | CCC | ATC | CAG | TTT | GTC | CCC | ACC | ATC | TCC | ACT | CTG | CCC | CAT | GGG | CTC | 720 |
|---|---|---|---|---|---|---|---|---|---|---|---|---|---|---|---|---|
| Gly<br>225 | Pro | Ile | Gln | Phe | Val<br>230 | Pro | Thr | Ile | Ser | Thr<br>235 | Leu | Pro | His | Gly | Leu<br>240 | |

| TGG | CAA | ATC | TCT | GAG | GCT | GGA | ACA | GGG | GTC | TCC | AGT | ATA | TTC | ATC | TAC | 768 |
|---|---|---|---|---|---|---|---|---|---|---|---|---|---|---|---|---|
| Trp | Gln | Ile | Ser | Glu<br>245 | Ala | Gly | Thr | Gly | Val<br>250 | Ser | Ser | Ile | Phe | Ile<br>255 | Tyr | |

| CAT | GGT | GAG | GTG | CCC | CAG | GCC | AGC | CAA | GTA | CCC | CCT | CCC | AGT | GGA | TTC | 816 |
|---|---|---|---|---|---|---|---|---|---|---|---|---|---|---|---|---|
| His | Gly | Glu | Val<br>260 | Pro | Gln | Ala | Ser | Gln<br>265 | Val | Pro | Pro | Pro | Ser<br>270 | Gly | Phe | |

| ACT | GTC | CAC | GGC | CTC | CCA | ACA | TCT | CCA | GAC | CGG | CCA | GGC | TCC | ACC | AGC | 864 |
|---|---|---|---|---|---|---|---|---|---|---|---|---|---|---|---|---|
| Thr | Val | His<br>275 | Gly | Leu | Pro | Thr | Ser<br>280 | Pro | Asp | Arg | Pro | Gly<br>285 | Ser | Thr | Ser | |

| CCC | TTC | GCT | CCA | TCA | GCC | ACT | GAC | CTG | CCC | AGC | ATG | CCT | GAA | CCT | GCC | 912 |
|---|---|---|---|---|---|---|---|---|---|---|---|---|---|---|---|---|
| Pro | Phe<br>290 | Ala | Pro | Ser | Ala | Thr<br>295 | Asp | Leu | Pro | Ser | Met<br>300 | Pro | Glu | Pro | Ala | |

| CTG | ACC | TCC | CGA | GCA | AAC | ATG | ACA | GAG | CAC | AAG | ACG | TCC | CCC | ACC | CAA | 960 |
|---|---|---|---|---|---|---|---|---|---|---|---|---|---|---|---|---|
| Leu<br>305 | Thr | Ser | Arg | Ala | Asn<br>310 | Met | Thr | Glu | His | Lys<br>315 | Thr | Ser | Pro | Thr | Gln<br>320 | |

| TGC | CCG | GCA | GCT | GGA | GAG | GTC | TCC | AAC | AAG | CTT | CCA | AAA | TGG | CCT | GAG | 1008 |
|---|---|---|---|---|---|---|---|---|---|---|---|---|---|---|---|---|
| Cys | Pro | Ala | Ala | Gly<br>325 | Glu | Val | Ser | Asn | Lys<br>330 | Leu | Pro | Lys | Trp | Pro<br>335 | Glu | |

| CCG | GTG | GAG | CAG | TTC | TAC | CGC | TCA | CTG | CAG | GAC | ACG | TAT | GGT | GCC | GAG | 1056 |

|  |  |  |  |  |  |  |  |  |  |  |  |  |  |  |  |  |
|---|---|---|---|---|---|---|---|---|---|---|---|---|---|---|---|---|
| Pro | Val | Glu | Gln<br>340 | Phe | Tyr | Arg | Ser | Leu<br>345 | Gln | Asp | Thr | Tyr<br>350 | Gly | Ala | Glu | |
| CCC | GCA | GGC | CCG | GAT | GGC | ATC | CTA | GTG | GAG | GTG | GAT | CTG | GTG | CAG | GCC | 1104 |
| Pro | Ala | Gly<br>355 | Pro | Asp | Gly | Ile<br>360 | Leu | Val | Glu | Val | Asp<br>365 | Leu | Val | Gln | Ala | |
| AGG | CTG | GAG | AGG | AGC | AGC | AGC | AAG | AGC | CTG | GAG | CGG | GAA | CTG | GCC | ACC | 1152 |
| Arg | Leu<br>370 | Glu | Arg | Ser | Ser | Ser<br>375 | Lys | Ser | Leu | Glu | Arg<br>380 | Glu | Leu | Ala | Thr | |
| CCG | GAC | TGG | GCA | GAA | CGG | CAG | CTG | GCC | CAA | GGA | GGC | CTG | GCT | GAG | GTG | 1200 |
| Pro<br>385 | Asp | Trp | Ala | Glu | Arg<br>390 | Gln | Leu | Ala | Gln | Gly<br>395 | Gly | Leu | Ala | Glu | Val<br>400 | |
| CTG | TTG | GCT | GCC | AAG | GAG | CAC | CGG | CGG | CCG | CGT | GAG | ACA | CGA | GTG | ATT | 1248 |
| Leu | Leu | Ala | Ala | Lys<br>405 | Glu | His | Arg | Arg | Pro<br>410 | Arg | Glu | Thr | Arg | Val<br>415 | Ile | |
| GCT | GTG | CTG | GGC | AAA | GCT | GGT | CAG | GGC | AAG | AGC | TAT | TGG | GCT | GGG | GCA | 1296 |
| Ala | Val | Leu | Gly<br>420 | Lys | Ala | Gly | Gln | Gly<br>425 | Lys | Ser | Tyr | Trp | Ala<br>430 | Gly | Ala | |
| GTG | AGC | CGG | GCC | TGG | GCT | TGT | GGC | CGG | CTT | CCC | CAG | TAC | GAC | TTT | GTC | 1344 |
| Val | Ser | Arg<br>435 | Ala | Trp | Ala | Cys | Gly<br>440 | Arg | Leu | Pro | Gln | Tyr<br>445 | Asp | Phe | Val | |
| TTC | TCT | GTC | CCC | TGC | CAT | TGC | TTG | AAC | CGT | CCG | GGG | GAT | GCC | TAT | GGC | 1392 |
| Phe | Ser | Val<br>450 | Pro | Cys | His | Cys<br>455 | Leu | Asn | Arg | Pro | Gly<br>460 | Asp | Ala | Tyr | Gly | |
| CTG | CAG | GAT | CTG | CTC | TTC | TCC | CTG | GGC | CCA | CAG | CCA | CTC | GTG | GCG | GCC | 1440 |
| Leu<br>465 | Gln | Asp | Leu | Leu | Phe<br>470 | Ser | Leu | Gly | Pro | Gln<br>475 | Pro | Leu | Val | Ala | Ala<br>480 | |
| GAT | GAG | GTT | TTC | AGC | CAC | ATC | TTG | AAG | AGA | CCT | GAC | CGC | GTT | CTG | CTC | 1488 |
| Asp | Glu | Val | Phe | Ser<br>485 | His | Ile | Leu | Lys | Arg<br>490 | Pro | Asp | Arg | Val | Leu<br>495 | Leu | |
| ATC | CTA | GAC | GCC | TTC | GAG | GAG | CTG | GAA | GCG | CAA | GAT | GGC | TTC | CTG | CAC | 1536 |
| Ile | Leu | Asp | Ala<br>500 | Phe | Glu | Glu | Leu | Glu<br>505 | Ala | Gln | Asp | Gly | Phe<br>510 | Leu | His | |
| AGC | ACG | TGC | GGA | CCG | GCA | CCG | GCG | GAG | CCC | TGC | TCC | CTC | CGG | GGG | CTG | 1584 |
| Ser | Thr | Cys<br>515 | Gly | Pro | Ala | Pro | Ala<br>520 | Glu | Pro | Cys | Ser | Leu<br>525 | Arg | Gly | Leu | |
| CTG | GCC | GGC | CTT | TTC | CAG | AAG | AAG | CTG | CTC | CGA | GGT | TGC | ACC | CTC | CTC | 1632 |
| Leu | Ala | Gly<br>530 | Leu | Phe | Gln | Lys<br>535 | Lys | Leu | Leu | Arg | Gly<br>540 | Cys | Thr | Leu | Leu | |
| CTC | ACA | GCC | CGG | CCC | CGG | GGC | CGC | CTG | GTC | CAG | AGC | CTG | AGC | AAG | GCC | 1680 |
| Leu<br>545 | Thr | Ala | Arg | Pro | Arg<br>550 | Gly | Arg | Leu | Val | Gln<br>555 | Ser | Leu | Ser | Lys | Ala<br>560 | |
| GAC | GCC | CTA | TTT | GAG | CTG | TCC | GGC | TTC | TCC | ATG | GAG | CAG | GCC | CAG | GCA | 1728 |
| Asp | Ala | Leu | Phe | Glu<br>565 | Leu | Ser | Gly | Phe | Ser<br>570 | Met | Glu | Gln | Ala | Gln<br>575 | Ala | |
| TAC | GTG | ATG | CGC | TAC | TTT | GAG | AGC | TCA | GGG | ATG | ACA | GAG | CAC | CAA | GAC | 1776 |
| Tyr | Val | Met | Arg<br>580 | Tyr | Phe | Glu | Ser | Ser<br>585 | Gly | Met | Thr | Glu | His<br>590 | Gln | Asp | |
| AGA | GCC | CTG | ACG | CTC | CTC | CGG | GAC | CGG | CCA | CTT | CTT | CTC | AGT | CAC | AGC | 1824 |
| Arg | Ala | Leu<br>595 | Thr | Leu | Leu | Arg | Asp<br>600 | Arg | Pro | Leu | Leu | Leu<br>605 | Ser | His | Ser | |
| CAC | AGC | CCT | ACT | TTG | TGC | CGG | GCA | GTG | TGC | CAG | CTC | TCA | GAG | GCC | CTG | 1872 |
| His | Ser<br>610 | Pro | Thr | Leu | Cys | Arg<br>615 | Ala | Val | Cys | Gln | Leu<br>620 | Ser | Glu | Ala | Leu | |
| CTG | GAG | CTT | GGG | GAG | GAC | GCC | AAG | CTG | CCC | TCC | ACG | CTC | ACG | GGA | CTC | 1920 |
| Leu | Glu | Leu | Gly<br>625 | Glu | Asp | Ala | Lys<br>630 | Leu | Pro | Ser | Thr<br>635 | Leu | Thr | Gly | Leu<br>640 | |
| TAT | GTC | GGC | CTG | CTG | GGC | CGT | GCA | GCC | CTC | GAC | AGC | CCC | CCC | GGG | GCC | 1968 |
| Tyr | Val | Gly | Leu | Leu<br>645 | Gly | Arg | Ala | Ala | Leu<br>650 | Asp | Ser | Pro | Pro<br>655 | Gly | Ala | |
| CTG | GCA | GAG | CTG | GCC | AAG | CTG | GCC | TGG | GAG | CTG | GGC | CGC | AGA | CAT | CAA | 2016 |

-continued

```
Leu Ala Glu Leu Ala Lys Leu Ala Trp Glu Leu Gly Arg Arg His Gln
        660                 665                 670

AGT ACC CTA CAG GAG GAC CAG TTC CCA TCC GCA GAC GTG AGG ACC TGG     2064
Ser Thr Leu Gln Glu Asp Gln Phe Pro Ser Ala Asp Val Arg Thr Trp
    675                 680                 685

GCG ATG GCC AAA GGC TTA GTC CAA CAC CCA CCG CGG GCC GCA GAG TCC     2112
Ala Met Ala Lys Gly Leu Val Gln His Pro Pro Arg Ala Ala Glu Ser
    690                 695                 700

GAG CTG GCC TTC CCC AGC TTC CTC CTG CAA TGC TTC CTG GGG GCC CTG     2160
Glu Leu Ala Phe Pro Ser Phe Leu Leu Gln Cys Phe Leu Gly Ala Leu
705                 710                 715                 720

TGG CTG GCT CTG AGT GGC GAA ATC AAG GAC AAG GAG CTC CCG CAG TAC     2208
Trp Leu Ala Leu Ser Gly Glu Ile Lys Asp Lys Glu Leu Pro Gln Tyr
                725                 730                 735

CTA GCA TTG ACC CCA AGG AAG AAG AGG CCC TAT GAC AAC TGG CTG GAG     2256
Leu Ala Leu Thr Pro Arg Lys Lys Arg Pro Tyr Asp Asn Trp Leu Glu
            740                 745                 750

GGC GTG CCA CGC TTT CTG GCT GGG CTG ATC TTC CAG CCT CCC GCC CGC     2304
Gly Val Pro Arg Phe Leu Ala Gly Leu Ile Phe Gln Pro Pro Ala Arg
        755                 760                 765

TGC CTG GGA GCC CTA CTC GGG CCA TCG GCG GCT GCC TCG GTG GAC AGG     2352
Cys Leu Gly Ala Leu Leu Gly Pro Ser Ala Ala Ala Ser Val Asp Arg
    770                 775                 780

AAG CAG AAG GTG CTT GCG AGG TAC CTG AAG CGG CTG CAG CCG GGG ACA     2400
Lys Gln Lys Val Leu Ala Arg Tyr Leu Lys Arg Leu Gln Pro Gly Thr
785                 790                 795                 800

CTG CGG GCG CGG CAG CTG CTT GAG CTG CTG CAC TGC GCC CAC GAG GCC     2448
Leu Arg Ala Arg Gln Leu Leu Glu Leu Leu His Cys Ala His Glu Ala
                805                 810                 815

GAG GAG GCT GGA ATT TGG CAG CAC GTG GTA CAG GAG CTC CCC GGC CGC     2496
Glu Glu Ala Gly Ile Trp Gln His Val Val Gln Glu Leu Pro Gly Arg
            820                 825                 830

CTC TCT TTT CTG GGC ACC CGC CTC ACG CCT CCT GAT GCA CAT GTA CTG     2544
Leu Ser Phe Leu Gly Thr Arg Leu Thr Pro Pro Asp Ala His Val Leu
        835                 840                 845

GGC AAG GCC TTG GAG GCG GCG GGC CAA GAC TTC TCC CTG GAC CTC CGC     2592
Gly Lys Ala Leu Glu Ala Ala Gly Gln Asp Phe Ser Leu Asp Leu Arg
    850                 855                 860

AGC ACT GGC ATT TGC CCC TCT GGA TTG GGG AGC CTC GTG GGA CTC AGC     2640
Ser Thr Gly Ile Cys Pro Ser Gly Leu Gly Ser Leu Val Gly Leu Ser
865                 870                 875                 880

TGT GTC ACC CGT TTC AGG GCT GCC TTG AGC GAC ACG GTG GCG CTG TGG     2688
Cys Val Thr Arg Phe Arg Ala Ala Leu Ser Asp Thr Val Ala Leu Trp
                885                 890                 895

GAG TCC CTG CGG CAG CAT GGG GAG ACC AAG CTA CTT CAG GCA GCA GAG     2736
Glu Ser Leu Arg Gln His Gly Glu Thr Lys Leu Leu Gln Ala Ala Glu
            900                 905                 910

GAG AAG TTC ACC ATC GAG CCT TTC AAA GCC AAG TCC CTG AAG GAT GTG     2784
Glu Lys Phe Thr Ile Glu Pro Phe Lys Ala Lys Ser Leu Lys Asp Val
        915                 920                 925

GAA GAC CTG GGA AAG CTT GTG CAG ACT CAG AGG ACG AGA AGT TCC TCG     2832
Glu Asp Leu Gly Lys Leu Val Gln Thr Gln Arg Thr Arg Ser Ser Ser
    930                 935                 940

GAA GAC ACA GCT GGG GAG CTC CCT GCT GTT CGG GAC CTA AAG AAA CTG     2880
Glu Asp Thr Ala Gly Glu Leu Pro Ala Val Arg Asp Leu Lys Lys Leu
945                 950                 955                 960

GAG TTT GCG CTG GGC CCT GTC TCA GGC CCC CAG GCT TTC CCC AAA CTG     2928
Glu Phe Ala Leu Gly Pro Val Ser Gly Pro Gln Ala Phe Pro Lys Leu
                965                 970                 975

GTG CGG ATC CTC ACG GCC TTT TCC TCC CTG CAG CAT CTG GAC CTG GAT     2976
```

```
Val Arg Ile Leu Thr Ala Phe Ser Ser Leu Gln His Leu Asp Leu Asp
            980                 985                990

GCG CTG AGT GAG AAC AAG ATC GGG GAC GAG GGT GTC TCG CAG CTC TCA         3024
Ala Leu Ser Glu Asn Lys Ile Gly Asp Glu Gly Val Ser Gln Leu Ser
            995             1000            1005

GCC ACC TTC CCC CAG CTG AAG TCC TTG GAA ACC CTC AAT CTG TCC CAG         3072
Ala Thr Phe Pro Gln Leu Lys Ser Leu Glu Thr Leu Asn Leu Ser Gln
        1010            1015            1020

AAC AAC ATC ACT GAC CTG GGT GCC TAC AAA CTC GCC GAG GCC CTG CCT         3120
Asn Asn Ile Thr Asp Leu Gly Ala Tyr Lys Leu Ala Glu Ala Leu Pro
1025            1030            1035            1040

TCG CTC GCT GCA TCC CTG CTC AGG CTA AGC TTG TAC AAT AAC TGC ATC         3168
Ser Leu Ala Ala Ser Leu Leu Arg Leu Ser Leu Tyr Asn Asn Cys Ile
            1045            1050            1055

TGC GAC GTG GGA GCC GAG AGC TTG GCT CGT GTG CTT CCG GAC ATG GTG         3216
Cys Asp Val Gly Ala Glu Ser Leu Ala Arg Val Leu Pro Asp Met Val
            1060            1065            1070

TCC CTC CGG GTG ATG GAC GTC CAG TAC AAC AAG TTC ACG GCT GCC GGG         3264
Ser Leu Arg Val Met Asp Val Gln Tyr Asn Lys Phe Thr Ala Ala Gly
        1075            1080            1085

GCC CAG CAG CTC GCT GCC AGC CTT CGG AGG TGT CCT CAT GTG GAG ACG         3312
Ala Gln Gln Leu Ala Ala Ser Leu Arg Arg Cys Pro His Val Glu Thr
        1090            1095            1100

CTG GCG ATG TGG ACG CCC ACC ATC CCA TTC AGT GTC CAG GAA CAC CTG         3360
Leu Ala Met Trp Thr Pro Thr Ile Pro Phe Ser Val Gln Glu His Leu
1105            1110            1115            1120

CAA CAA CAG GAT TCA CGG ATC AGC CTG AGA TGA                             3393
Gln Gln Gln Asp Ser Arg Ile Ser Leu Arg  *
            1125            1130
```

METHODS OF IDENTIFYING COMPOUNDS USEFUL FOR TREATING AUTOIMMUNE DISEASES

BACKGROUND OF THE INVENTION

This invention relates to autoimmune diseases.

The major histocompatability (MHC) class II molecules are expressed on the surfaces of antigen-presenting cells and B lymphocytes. By binding antigens and presenting the antigens to T cells, the MHC class II molecules are involved in triggering an immune response. Thus, the level of expression of the MHC class II molecules affects the induction of an immune response.

The genes which encode the α and β polypeptides of the MHC class II antigens are located at the HLA-D (histocompatability leukocyte antigen-D) region of the chromosome. Isotypes of the class II genes include those which are designated HLA-DR, HLA-DQ, and HLA-DP. Within these genes, there is substantial allelic polymorphism; for example, HLA-DR alleles include DR1, DR2, DR3, and DR4. In addition, subtypes of these alleles exist; for example, subtypes of DR4 include Dw4, Dw10, Dw13, Dw14, and Dw15.

Several autoimmune diseases are associated with expression of particular alleles of the MHC class II genes. Approximately 93% of patients afflicted with rheumatoid arthritis express HLA-DR1, HLA-DR4, or both (McDermott et al., Bulletin on the Rheumatic Diseases, 38:1-10; see Table 1).

TABLE 1

Population studies of the HLA associations of rheumatoid arthritis

| Population | HLA Antigen | Patients (%) | Controls (%) | Relative Risk |
|---|---|---|---|---|
| White Americans | Dw4 | 54 | 16 | 6 |
| White Americans | DR4 | 70 | 28 | 6 |
| Black Americans | DR4 | 46 | 14 | 5 |
| Japanese | DR4 | 67 | 41 | 3 |
| Mexican | DR4 | 26 | 3 | 11 |
| Asian Indian (in UK) | DR4 | 17 | 14 | 1 |
| | DR1 | 60 | 17 | 7 |
| Israeli Jews | DR1 | 31 | 11 | 4 |
| Israeli Jews | DR4 | 48 | 38 | 1.5 |
| | DR1 | 16 | 16 | 1 |
| Yakima Indians | DR4 | 41 | 38 | 1 |

Other autoimmune diseases also are linked to expression of particular alleles. For example, Felty's syndrome, Sjögren's syndrome, systemic lupus erythematosus, and the development of toxicities to gold and penicillamine are associated with various HLA-DR alleles (McDermott et al., Bulletin on the Rheumatic Diseases, 38:1-10; see Table 2).

TABLE 2

HLA associations of syndromes associated with RA, toxicity to penicillamine and gold, and myasthenia gravis

| Syndrome | HLA Antigen | Patients % | Controls % | Relative Risk |
|---|---|---|---|---|
| Felty's syndrome | DR4 | 96 | 36 | 43 |
| Sjögren's syndrome | | | | |
| Primary | B8 | 59 | 24 | 5 |
| | DR3 | 64 | 31 | 4 |
| Sjögren's syndrome | | | | |
| Secondary to RA | DR4 | 65 | 31 | 4 |
| Secondary to SLE | DR2 | 40 | 24 | 2 |
| Side effects to drugs | | | | |
| Gold-proteinuria | DR3 | 79 | 10 (treated controls) | 34 |
| Gold-induced harmatocytotoxicity | DR3 | 88 | 17 | 36 |
| | B8 | 88 | 25 | 22 |
| Penicillamine-induced thrombocytopenia | DR4 | 93 | 71 | 5 |
| myasthenia gravis | DR1 | 70 | 18 | 11 |
| | B35 DR1 | 50 | 5 | 19 |

As another example, pauciarticular juvenile rheumatoid arthritis is associated with HLA-DPB2.1 (Begovich et al., 1989, PNAS 86:9489-9493). Approximately 70% of patients with insulin-dependent diabetes mellitus express HLA-DQ3.2B, DQA1, or DQB1, and susceptibility to the autoimmune dermatologic disease pemphigus vulgaris is linked to expression of HLA-DQB1.3 (Scharf et al., 1989, PNAS 86:6215-6219).

Activation of transcription of the MHC Class II genes is dependent upon the transactivator CIITA (Steimle et al., 1993, Cell 75:135-146).

SUMMARY OF THE INVENTION

We have discovered that a portion of CIITA is sufficient, in the absence of the remainder of the protein and in the presence of an otherwise complete transcription system, to activate transcription. We refer to this domain as the CIITA transcription activation domain, and we have established that it provides useful information for identifying compounds which inhibit CIITA-dependent transcription. Such compounds are potential autoimmune disease therapeutics by virtue of their ability to inhibit transcription of the MHC class II genes. We have also discovered that a second portion of CIITA is sufficient, in the absence of the remainder of the protein and in the presence of an otherwise complete transcription system, to mediate the interaction of CIITA and its target protein in the cellular transcription machinery and to activate all MHC class II promoters. We refer to this domain as the CIITA interaction domain, and compounds which inhibit binding of this domain to its target protein can inhibit CIITA-dependent transcription and thus are potential autoimmune disease therapeutics. We also have discovered that a mutant of CIITA (referred to herein as clone 13 CIITA) activates transcription of a subset of the MHC class II genes. We refer to this mutant as isotype-specific; the transcription activation and interaction domains of isotype-specific CIITA proteins are useful for identifying compounds which are isotype-specific inhibitors of transcription.

Accordingly, the invention features methods which employ the CIITA activation domain or interaction domain to determine whether a compound is a potential autoimmune disease therapeutic. The presence or absence of a functional CIITA activation domain or a functional CIITA interaction domain can be established using the transcription measuring techniques described below. In one method, the ability of a compound to inhibit transcription of a reporter gene is measured, with inhibition of transcription indicating that the compound is a potential autoimmune disease therapeutic. In another method, the ability of a compound to inhibit binding of the CIITA interaction domain to its target protein is measured, with inhibition of binding indicating that the compound is a potential autoimmune disease therapeutic. In still another method, the ability of the CIITA interaction domain to mediate transcription is measured in the absence of a CIITA transcription activation domain and in the presence of the transcription activation domain of another protein. Compounds which inhibit the function of the interaction domain are potential autoimmune disease therapeutics. By measuring the ability of the wild-type CIITA interaction domain to mediate transcription in the presence of compounds to be tested and by monitoring for the expression of each isotype, this method allows for the identification of compounds which are isotype-specific inhibitors of transcription. In the presence of an isotype-specific inhibitor, the wild-type CIITA interaction domain mediates the transcription of only a subset of MHC class II genes.

The invention further features methods which employ isotype-specific CIITA interaction and transcription activation domains to identify compounds which are isotype-specific inhibitors of transcription. In these methods compounds are tested for their ability to differentially affect transcription mediated by wild-type and isotype-specific CIITA interaction and transcription activation domains. Such isotype-specific inhibitors are useful for selectively affecting the immune system.

Inhibition of transcription can be measured in vivo, in vitro, or in cell-based assays. A wide variety of techniques for measuring the activity of a transcription activation domain are known in the art (see, e.g., Keegan et al., 1986, Science 23: 699; Ma et al., 1987, Cell 48: 847; Lin et al., 1988, Cell 54: 659; Sadowski et al., 1988, Nature 335: 563; Roberts et al., 1993, Nature 363: 741; and Ma et al., 1988, Cell 55: 443). These and other transcription assays can be modified for the purpose of identifying compounds which inhibit CIITA activation of transcription. This can be accomplished by substituting the newly-identified CIITA transcription activation domain for the activation domain used in a previously described assay. Compounds which inhibit CIITA activation of transcription can be identified by simply adding the compounds to the transcription reaction and determining whether the compound inhibits transcription. Such compounds are potential autoimmune disease therapeutics.

In preferred embodiments, potential autoimmune disease therapeutics are identified by:
  a) providing a fusion protein which includes a CIITA transcription activation domain (without a functional CIITA interaction domain) fused to a DNA binding protein (e.g., the DNA binding/dimerization domain of LexA or the DNA binding domain of GAL4);
  b) providing the fusion protein in a transcription system (e.g., in vitro or in a prokaryotic or eukaryotic cell such as a bacterial cell, a yeast cell, a plant cell, or a mammalian cell), with the transcription system having DNA which has a regulatory sequence (e.g., on a plasmid or on a chromosome) to which the fusion protein binds, and the regulatory sequence being operably linked to a reporter gene (e.g., a gene encoding β-galactosidase, CAT, GUS, luciferase, human growth hormone, or alkaline phosphatase);
  c) measuring the level of transcription of the reporter gene (e.g., by using standard techniques to measure the level or activity of an RNA or protein product of the reporter gene. For example, transcription of the lacZ gene can be measured by growing the cells in or on media containing X-gal, and measuring the amount of blue chromophore produced); and
  d) performing steps a–c, above, in the presence of the compound to be tested, a decrease in the level of transcription (relative to levels seen in the absence of the compound) indicating that the compound inhibits CIITA activation of transcription and therefore is a potential autoimmune disease therapeutic.

In other preferred embodiments, the CIITA interaction domain is used to identify potential autoimmune disease therapeutics. These methods involve:
  a) providing a fusion protein which includes a CIITA interaction domain fused to a transcription activation domain other than that of CIITA (e.g., the transcription activation domain of Herpes Simplex Virus α-transducing factor (α-TDF));
  b) providing a CIITA-interacting target protein (e.g., the CIITA-interacting target protein of a human B cell);
  c) providing the fusion protein and the target protein in a transcription system (e.g., in vitro or in a prokaryotic or eukaryotic cell such as a bacterial cell, a yeast cell, a plant cell, or a mammalian cell such as a human B cell (e.g., clone 13, Raji, or RM3 cells)), with the transcription system having DNA which has a regulatory sequence including an MHC class II promoter sequence (e.g., on a plasmid or on a chromosome), and the regulatory sequence being operably linked to a reporter gene (e.g., an MHC class II gene, a gene encoding β-galactosidase, CAT, GUS, luciferase, human growth hormone, or alkaline phosphatase); and
  d) measuring the level of transcription of the reporter gene (e.g., by using standard techniques to measure the level or activity of an RNA or protein product of the reporter gene. For example, transcription of the MHC class II genes can be measured in a human B cell line by using FACS to assay an increase in expression of the MHC class II molecules on the cell surface.); and
  e) performing steps a–d, above, in the presence of the compound to be tested, a decrease in the level of transcription (relative to levels seen in the absence of the compound) indicating that the compound inhibits the ability of the CIITA interaction domain to mediate transcription and therefore is a potential autoimmune disease therapeutic. Compounds which are isotype-specific inhibitors of transcription can be identified by virtue of their ability to differentially inhibit expression of the MHC class II genes. For example, expression of the wild-type CIITA interaction domain clone 13 cells restores transcription of the HLA-DR, -DQ, and -DP isotypes. A compound which inhibits transcription, but not in an isotype-specific manner, will prevent restoration of expression of all 3 genes. In contrast, an isotype-specific inhibitor of transcription will interfere with restoration of expression of only a subset of the genes.

In other preferred embodiments, compounds which are potential autoimmune disease therapeutics are identified by:

a) providing a first fusion protein which includes a CIITA interaction domain (without a functional CIITA activation domain) fused to a DNA binding protein (e.g., the DNA binding/dimerization domain of LexA, or the DNA binding domain of GAL4);

b) providing the fusion protein in a transcription system (e.g., in vitro or in a prokaryotic or eukaryotic cell such as a bacterial cell, a yeast cell, a plant cell, or a mammalian cell), with the transcription system having DNA which has a regulatory sequence (e.g., on a plasmid or on a chromosome) to which the first fusion protein binds, and the regulatory sequence being operably linked to a reporter gene (e.g., a gene encoding β-galactosidase, CAT, GUS, luciferase, human growth hormone, or alkaline phosphatase);

c) providing a second fusion protein, the second fusion protein being characterized in that it includes a transcription activation domain (e.g., the transcription activation domain of B42) fused to a CIITA-interacting target protein as defined herein;

d) measuring the level of transcription of the reporter gene (e.g., by using standard techniques to measure the level or activity of an RNA or protein product of the reporter gene. For example, transcription of the lacZ gene can be measured by growing the cells in or on media containing X-gal, and measuring the amount of blue chromophore produced); and e) performing steps a–d, above, in the presence of the compound to be tested, a decrease in the level of transcription (relative to levels seen in the absence of the compound) indicating that the compound inhibits the ability of the CIITA interaction domain to bind its target protein and therefore is a potential autoimmune disease therapeutic. The compound which inhibits binding may function by a variety of methods including sterically interfering with binding or altering the structure of CIITA or its target protein. Although the exact mechanism by which the compound abolishes transcription may be unknown, the compound nevertheless is valuable as a therapeutic. Other methods of measuring protein-protein interactions can also be used to identify compounds which inhibit binding of the CIITA interaction domain to its target protein. Using standard molecular biology techniques, one skilled in the art can employ ELISAs, Southwestern blotting, filter- and membrane-bound proteins, or immobilized proteins to identify compounds which inhibit binding of the CIITA interaction domain to its target protein.

The invention also features a substantially purified polypeptide which includes a CIITA transcription activation domain without a functional CIITA interaction domain. Preferably, the polypeptide includes a greater than 50 amino acid sequence substantially identical to a greater than 50 amino acid sequence of amino acids 26–352 of the sequence shown in SEQ ID NO:1 (FIG. 1).

In a related aspect, the invention features substantially pure DNA (e.g., genomic DNA, cDNA, or synthetic DNA) encoding a CIITA transcription activation domain without encoding a functional CIITA interaction domain.

The invention further features a substantially purified polypeptide which includes a CIITA interaction domain without including a functional CIITA transcription activation domain. Preferably, the polypeptide includes a greater than 50 amino acid sequence substantially identical to a greater than 50 amino acid sequence of amino acids 301–1130 of the sequence shown in SEQ ID NO:1 (FIG. 1).

In a related aspect, the invention features substantially pure DNA (e.g., genomic DNA, cDNA, or synthetic DNA) encoding a CIITA interaction domain without encoding a functional CIITA transcription activation domain.

In addition, the invention features a substantially purified polypeptide which includes the interaction domain of the CIITA polypeptide of the clone 13 cell line (for a description of the cell line, see Ono et al., 1991, J. Exp. Med. 173:629–637). The clone 13 CIITA activates transcription of the MHC class II DQ gene but does not activate transcription of the MHC class II DR and DP genes. Preferably, the polypeptide includes a greater than 50 amino acid sequence substantially identical to a greater than 50 amino acids 301–1077 of the sequence shown in SEQ ID NO:1 (FIG. 1), while lacking amino acids 1–300 and 1078–1130 of the sequence shown in SEQ ID NO:1 (FIG. 1). In a related aspect, the invention includes a substantially pure DNA (e.g., genomic DNA, cDNA, or synthetic DNA) encoding the clone 13 CIITA.

Other isotype-specific CIITA mutants also are included in the invention, and the invention further features methods which employ the activation and interaction domains of isotype-specific mutants of CIITA to determine whether a compound is an isotype-specific inhibitor of transcription. A compound which is an isotype-specific inhibitors also is a potential autoimmune disease therapeutic. Such a compound is particularly useful as it can inhibit the transcription of particular genes known to be involved in autoimmune diseases while allowing expression of other MHC class II genes. Thus, an isotype-specific compound, when used as an autoimmune disease therapeutic, can avoid causing generalized immunosuppression.

A compound which is isotype-specific can be identified by using an isotype-specific CIITA in one of the inhibition assays described herein, and comparing the results with those obtained using wild-type CIITA or a CIITA mutant of a different isotype specificity. For example, a compound which inhibits transcription that is dependent upon wild-type CIITA, but not the clone 13 CIITA, is useful for inhibiting transcription of the MHC class II DR and DP genes. Because expression of DR1 and/or DR4 is associated with 93% of rheumatoid arthritis cases, a compound which specifically inhibits transcription of the DR genes is a strong candidate for a rheumatoid arthritis therapeutic. Similarly, two isotype-specific mutants of CIITA can be used to determine whether a compound is an isotype-specific inhibitor of transcription. For example, a comparative method can involve a first CIITA mutant which activates transcription of DR and DP, and a second CIITA mutant which activates transcription of only DP. A compound which inhibits the ability of the first mutant but not the second mutant is useful for selectively inhibiting the expression of DR.

By "class II transactivator gene" (CIITA gene) is meant a gene encoding an activator of transcription, with the gene having about 80% or greater sequence identity to the CIITA sequence of SEQ ID NO:1 (FIG. 1).

By "CIITA transcription activation domain" is meant a polypeptide having about 80% or greater sequence identity to amino acids 26–352 of the CIITA polypeptide shown in SEQ ID NO:1 (FIG. 1) without having a functional CIITA interaction domain.

By "CIITA interaction domain" is meant a polypeptide having about 80% or greater sequence identity to amino acids 301–1130 of the CIITA polypeptide shown in SEQ ID NO:1 (FIG. 1) without having a functional CIITA transcription activation domain. An example of a mutant CIITA interaction domain is the interaction domain of clone 13 CIITA, the DNA sequence of which is characterized, at least in part, by a deletion of nucleotides 3211–3214 of the wild-type CIITA sequence shown in SEQ ID NO:1 (FIG. 1) (this corresponds to nucleotides 3326–3329 of the cDNA sequence described previously (Steimle et al., infra)), resulting in a protein which is truncated by 53 amino acids relative to wild-type.

It will be understood that the CIITA transcription activation and interaction domains as defined herein overlap by about 51 amino acids. However, the region of overlap is not sufficient to constitute a functional transcription activation or interaction domain. Thus, a polypeptide having amino acids 26–352 and lacking amino acids 353–1130 of the sequence shown in SEQ ID NO:1 (FIG. 1) has a functional transcription activation domain but lacks a functional interaction domain. Similarly, a polypeptide having amino acids 301–1130 and lacking amino acids 1–300 of the sequence shown in SEQ ID NO:1 (FIG. 1) has a functional interaction domain, but lacks a functional transcription activation domain.

By "polypeptide" is meant any chain of amino acids, regardless of length or post-translational modification (e.g., glycosylation or phosphorylation).

By "operably linked" is meant that a gene and a regulatory sequence(s) are connected in such a way as to permit gene expression when the appropriate molecules (e.g., transcriptional activator proteins) are bound to the regulatory sequence(s).

By "reporter gene" is meant a gene whose expression may be assayed; such genes include, without limitation, the lacZ, chloramphenicol acetyltransferase (CAT), β-glucuronidase (GUS), and luciferase genes.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably at least 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "substantially pure polypeptide" is meant a polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, the desired protein. A substantially pure CIITA transcription activation domain or CIITA interaction domain can be obtained, for example, by extraction from a natural source (e.g., a human cell); by expression of a recombinant nucleic acid encoding a CIITA transcription activation domain or CIITA interaction domain; or by chemically synthesizing the polypeptide. Purity can be measured by any appropriate method (e.g., column chromatography, polyacrylamide gel electrophoresis, and HPLC analysis).

A protein is substantially free of naturally associated components when it is separated from those contaminants which accompany it in its natural state. Thus, a protein which is chemically synthesized, synthesized in vitro, or produced in a cellular system different from the cell from which it naturally originates will be substantially free from its naturally associated components. Accordingly, substantially pure polypeptides include those derived from eukaryotic organisms but synthesized in E. coli or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote (e.g., a yeast cell); or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

DETAILED DESCRIPTION

The drawings will first be described.

FIG. 1 is a listing of the nucleotide and predicted amino acid sequences of full length CIITA (SEQ ID NO: 1).

FIG. 2 is a schematic representation of the CIITA deletion mutants and the in vivo assay used to identify the CIITA transcription activation and interaction domains. The results of the transcription assays are also summarized in this FIG.

FIGS. 6A–E is a series of FACS profiles which shows that expression an α-TDF/CIITA fusion protein in clone 13 and RM3 cells restores expression of the MHC class II genes.

Figure 7A:
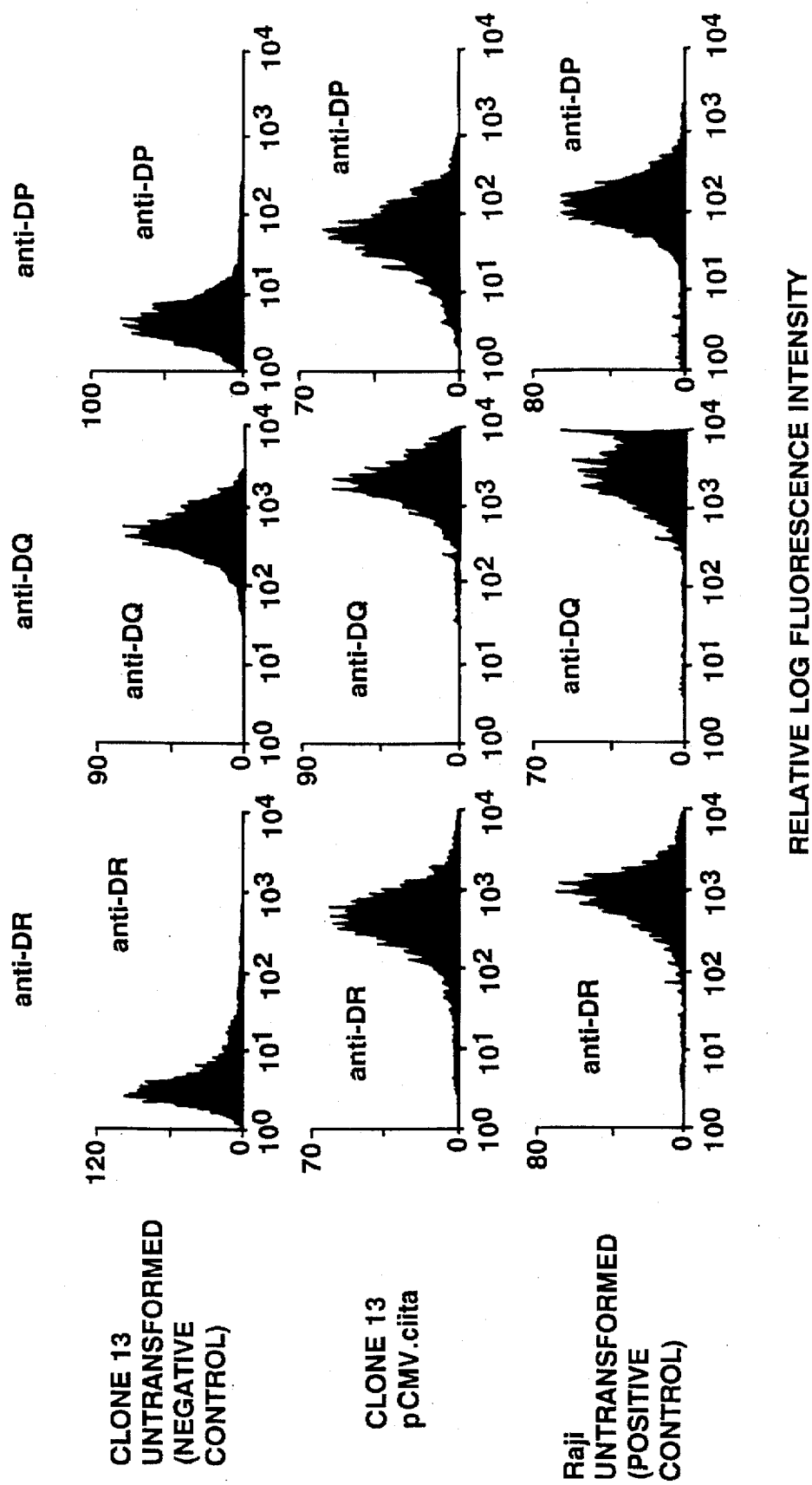
Figure 7B:
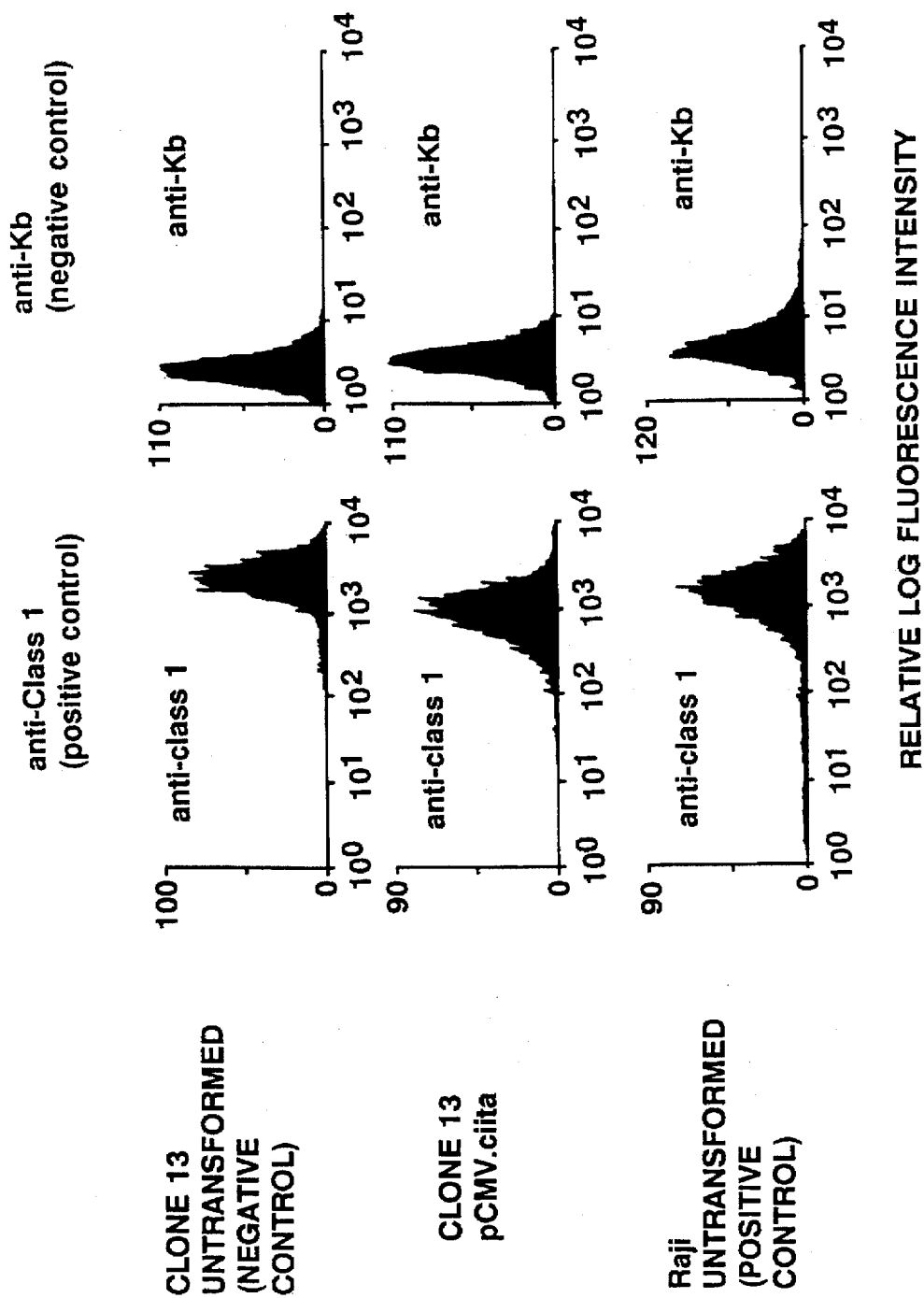
Figure 8A:
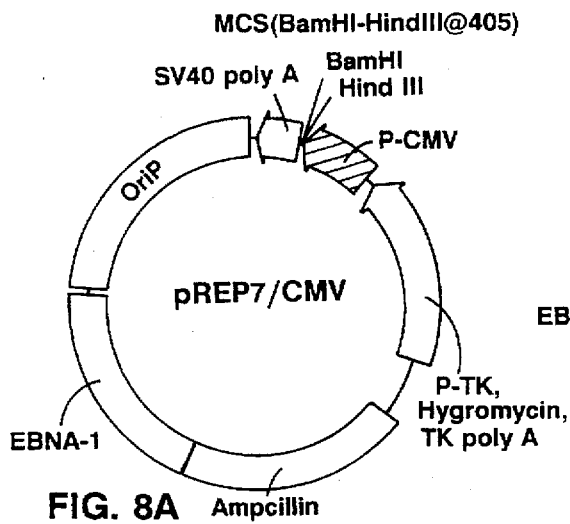
Figure 8B:
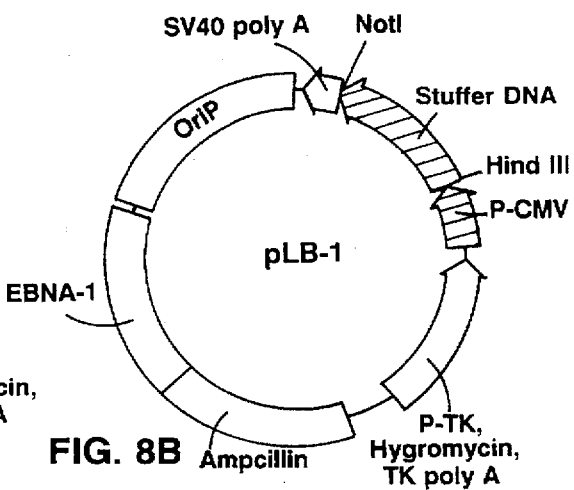
Figure 8C:
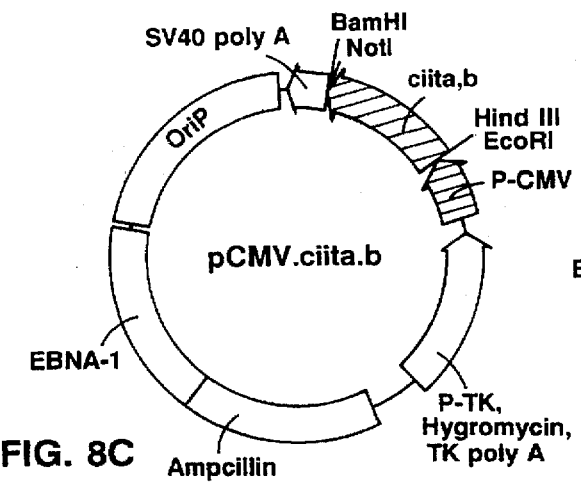
Figure 8D:
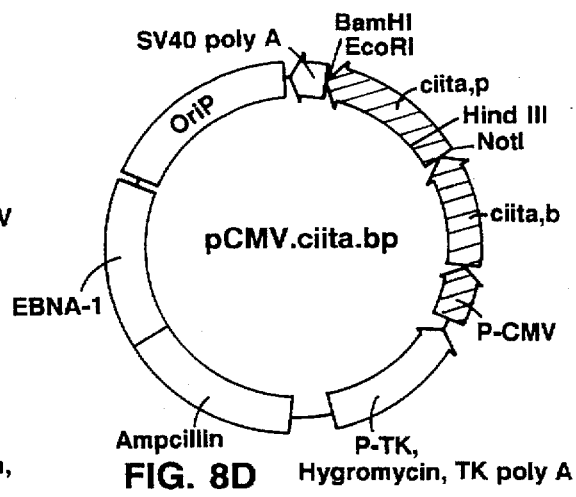
Figure 8E:
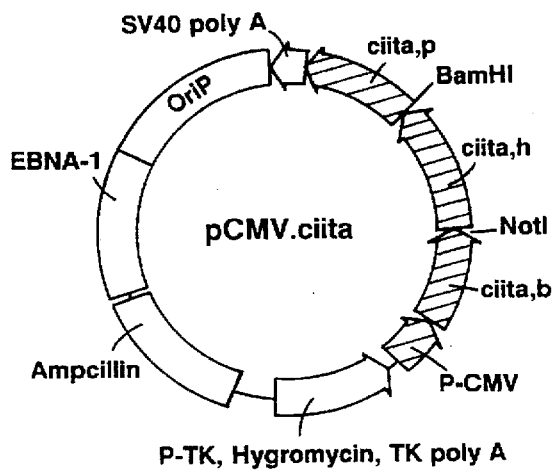
Figure 8F:
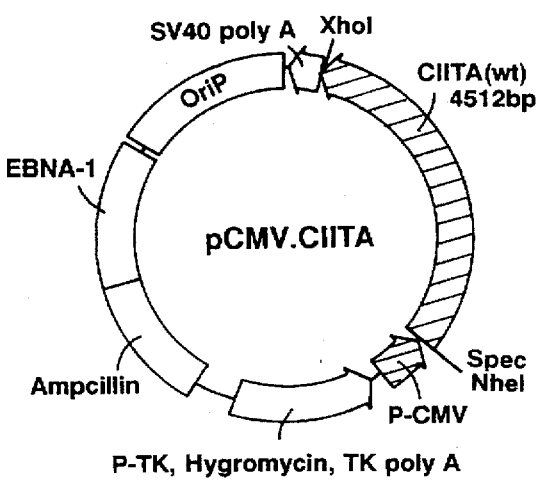

FIG. 7 is a series of FACS profiles which shows that expression of wild-type CIITA in clone 13 cells corrects the deficiency in the expression of the DR and DP isotypes and increases expression of DQ.

FIGS. 8A–F is a schematic representation of plasmids described herein.

THE CIITA TRANSCRIPTION ACTIVATION DOMAIN

We have identified, for the first time, a segment of CIITA that is sufficient, in the absence of the remainder of the CIITA protein and in the presence of an otherwise complete transcription system, to activate transcription. We refer to this segment as the transcription activation domain of CIITA. To identify this domain of CIITA, a series of plasmids was constructed (from the vector pEG202) to produce fusion proteins containing portions of CIITA attached to the N-terminal 202 amino acid dimerization and DNA binding domain of the *E. coli* repressor protein LexA. Methods for constructing these plasmids and other plasmids described herein are provided below under "Construction of Plasmids."

Yeast cells of the strain EGY48 (his3⁻ and ura3⁻) then were co-transformed with each LexA-CIITA construct, independently, and a lacZ reporter plasmid (pSH18-34). Expression of these plasmids in yeast was maintained by expression of the HIS3 gene from the LexA-CIITA plasmid, and expression of URA3 from pSH18-34. The regulatory sequences of the lacZ reporter plasmid included 8 LexA binding sites in place of the GAL1 upstream activating sequences (FIG. 2). In this assay, the LexA polypeptide served as a DNA-binding protein, bringing the CIITA polypeptides close to the site of transcription.

Figure 3:
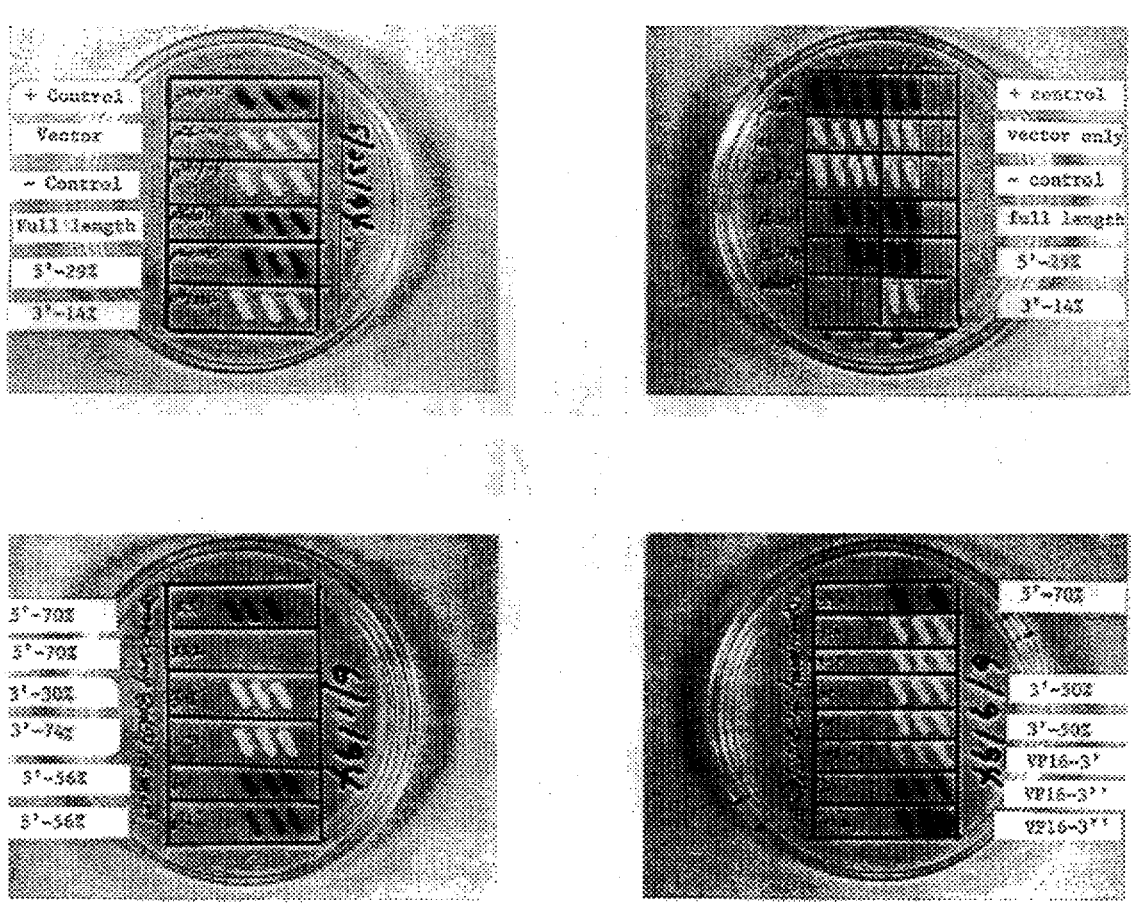
FIG. 3 is a photograph of the yeast cells used in the transcription assays to identify the CIITA transcription activation and interaction domains.
Figure 4:
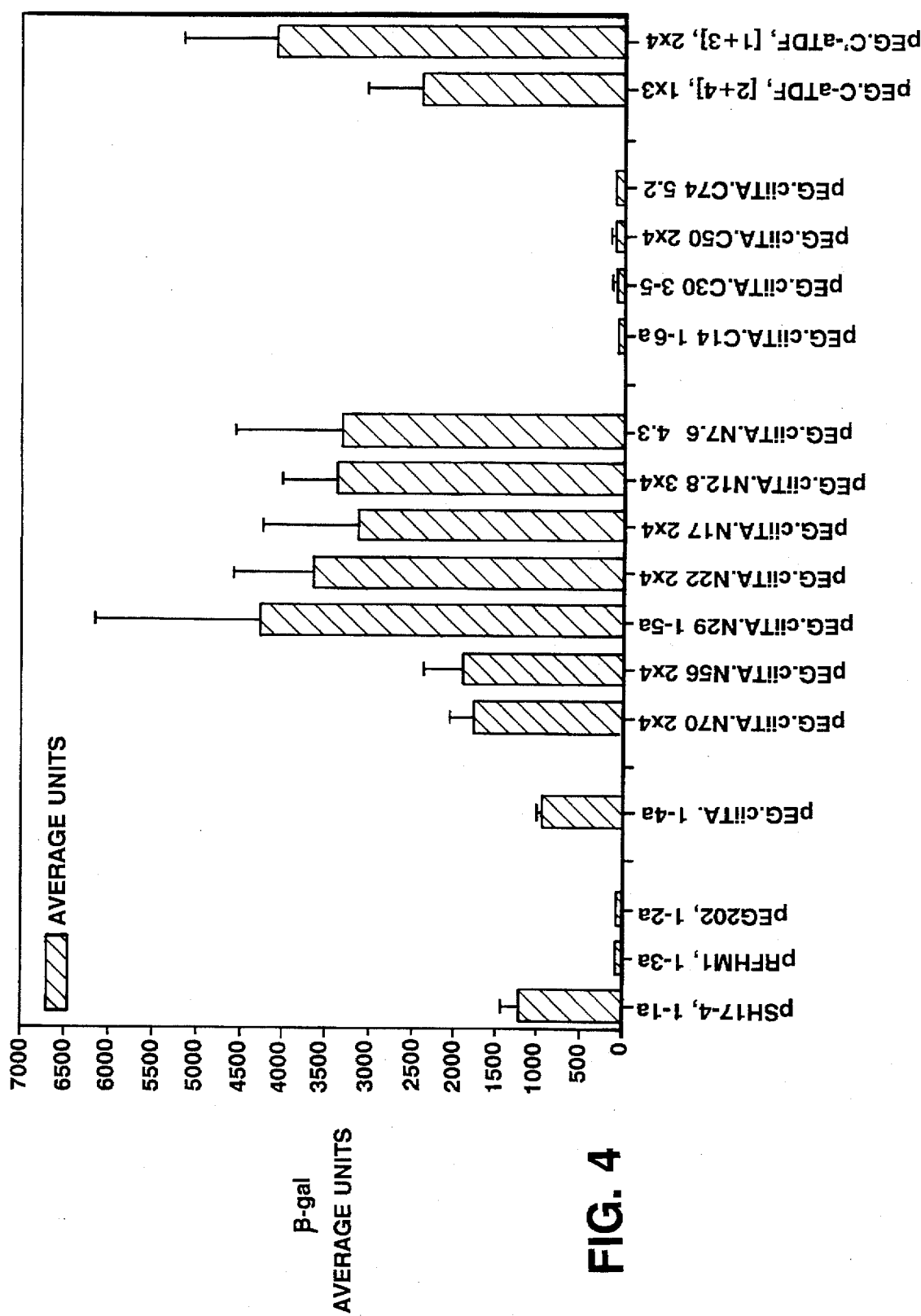
FIG. 4 is a histogram showing data obtained from a colorimetric assay used to measure transcription of the lacZ gene for identification of the CIITA transcription activation and interaction domains.

In the absence of a LexA fusion protein, yeast bearing the pSH18-34 reporter gene did not produce detectable quantities of β-galactosidase from the lacZ gene and appeared white on X-gal-containing media (FIG. 3; pHRFM1, a negative control). In addition, yeast bearing a plasmid expressing only the LexA N-terminal 202 amino acids or a fusion protein which is known not to have transcriptional activity (pSH17-4) failed to produce detectable quantities of β-galactosidase. In contrast, yeast strains having the LexA polypeptide fused to the transcription activation domain of CIITA (approximately the N-terminal 29%) induced synthesis of sufficient amounts of β-galactosidase that the host yeast cells appeared blue on X-gal-containing media (FIG. 3; pSH17-4, a positive control). In addition, quantitative colorimetric assays were performed by measuring the optical density of media containing the fusion proteins and o-nitrophenyl-β-galactoside (ONPG) (see FIG. 4) (Ausubel et al., In: Current Protocols in Molecular Biology, J. Wiley & Sons, 1994). Our data also indicate that a polypeptide which includes approximately 8% of the N-terminal region of CIITA is sufficient to activate transcription. This portion of CIITA contains the acidic portion of the transcription activation domain; if desired, the experiments performed with the N-terminal 29% can be compared with experiments performed with the N-terminal 8%. A polypeptide which includes approximately 29% of the N-terminal region of CIITA activates transcription at least as efficiently as the full length CIITA protein does. Thus, amino acids 26-352 and nucleotides 76 to 1,056 of the full length CIITA (see SEQ ID NO:1 (FIG. 1) represent the transcription activation domain (these numbers refer to the CIITA coding sequence, the beginning of which is at nucleotide 116 of the CIITA cDNA sequence (Steimle et al., infra)).

Use of the CIITA Transcription Activation Domain to Identify Autoimmune Disease Therapeutics The activation domain of CIITA can be used in a method of identifying compounds which inhibit CIITA-dependent transcription. Because CIITA is required for activation of MHC class II genes, compounds which specifically inhibit CIITA-dependent transcription are strong candidates for autoimmune disease therapeutics. Our discovery that a segment of CIITA (termed the CIITA transcription activation domain) is able to activate transcription in the absence of the remainder of the CIITA protein, and in the presence of an otherwise complete transcription system, facilitates the identification of compounds which inhibit transcription activation by CIITA.

Useful compounds are identified by their ability to inhibit CIITA-dependent transcription. To this end, the compound can be tested for inhibition of transcription in any transcription assay system which employs the CIITA activation domain. There now follows an example of an assay which can be used to identify compounds which inhibit CIITA-dependent transcription; compounds identified with this assay are candidates for autoimmune disease therapeutics. Other assays (e.g., those described by Keegan et al., 1986, Science 23: 699; Ma et al., 1987, Cell 48: 847; Lin et al., 1988, Cell 54: 659; Sadowski et al., 1988, Nature 335: 563; Roberts et al., 1993, Nature 363: 741; and Ma et al., 1988, Cell 55: 443) can be modified to employ the CIITA transcription activation domain which we have discovered. The CIITA transcription activation domain can simply be cloned into the appropriate vector, and thus other transcription assays are not excluded from this invention, the metes and bounds of which are determined by the claims below.

EXAMPLE 1

Identification of Compounds which Inhibit the CIITA Transcription Activation Domain To identify useful compounds, the host yeast strain EGY48 (his3⁻, ura3⁻, and leu⁻) is transformed with two plasmids. The first plasmid, pSH18-34, carries the GAL1 TATA transcription start site and a segment of the GAL1 coding sequence operably linked to the lacZ gene (Zervos et al., 1993, Cell 72: 223-232 and Gyuris et al., 1993, Cell 75: 791-803). This plasmid also carries 8 binding sites for LexA in place of the GAL1 upstream activating sequences, and it carries a URA3 selectable marker. The second plasmid, pEG.ciita.N29, is derived from the parental plasmid pEG202 and carries sequences which encode the CIITA transcription activation domain. This plasmid also carries a gene for a selectable marker (HIS3). and the DNA-binding and dimerization domains of LexA (amino acids 1-202). In control yeast strains, the second plasmid can be pSH17-4 (Gyuris et al., 1993, Cell 75:791-803) which encodes LexA fused to a transcription activation domain such as those of pHRFM1 or CDK2 (Zervos et al., 1993, Cell 72: 223-232 and Gyuris et al., 1993, Cell 75: 791-803).

Small cultures of the doubly-transformed yeast strains are mixed with the compounds to be screened and grown in a suitable medium (e.g., SGR, −his, −ura, +X-gal (80 mg/L)) under suitable conditions (e.g., at 30° C. with agitation overnight). The amount of blue chromophore produced is then determined (e.g., by measuring the optical density or by manually examining the cultures). Compounds which inhibit activation of transcription by the test plasmid (pEG.ciita.N29) but not the control plasmid (pSH17-4) can inhibit expression of the MHC class II molecules, and, therefore, are strong candidates for autoimmune disease therapeutics.

The CIITA Interaction Domain

The deletion analysis described above also indicated that a polypeptide which included amino acids 1-26 and 301-1130 (nucleotides 1-78 and 903-3390) of the full-length CIITA did not, alone, activate transcription (FIGS. 1, 2, and 3). Since this domain is not capable of activating transcription in the absence of a transcription activation domain (derived from CIITA or another activator of transcription), we conclude that this domain mediates transcription by binding to another component of the cellular transcription machinery (e.g., a polymerase or a DNA binding protein). Accordingly, amino acids 301-1130 (the C-terminal 74%) of CIITA have been termed the CIITA interaction domain. Although the CIITA interaction domain cannot, alone, activate transcription, compounds which inhibit binding of the interaction domain to its normal cellular target protein are useful for inhibiting transcription of CIITA and therefore are potential autoimmune disease therapeutics.

Use of the CIITA Interaction Domain to Restore MHC Class II Gene Expression

Figure 5:
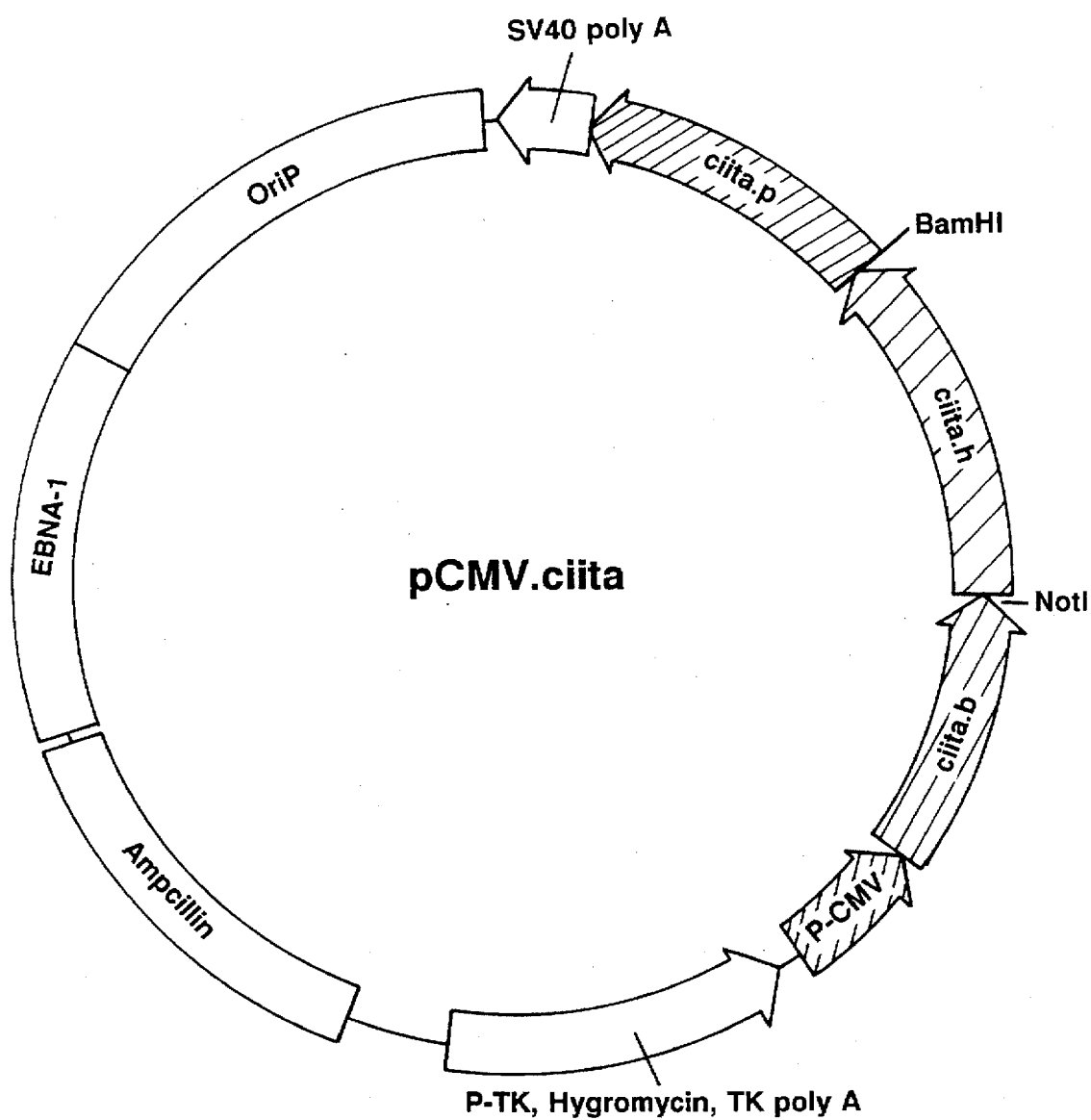
FIG. 5 is a schematic representation of plasmid pCMV.ciita.
Figure 6A:
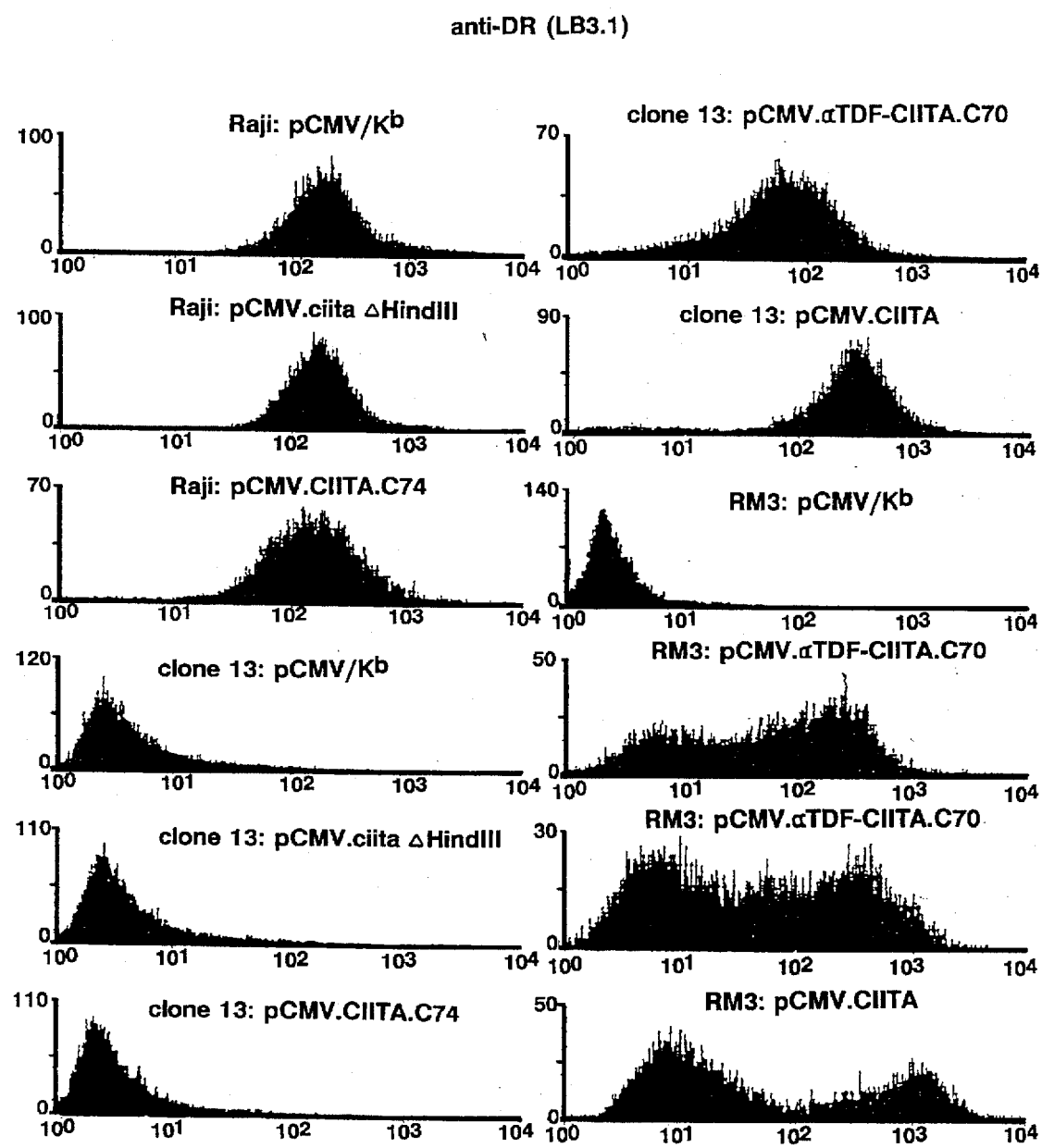
Figure 6B:
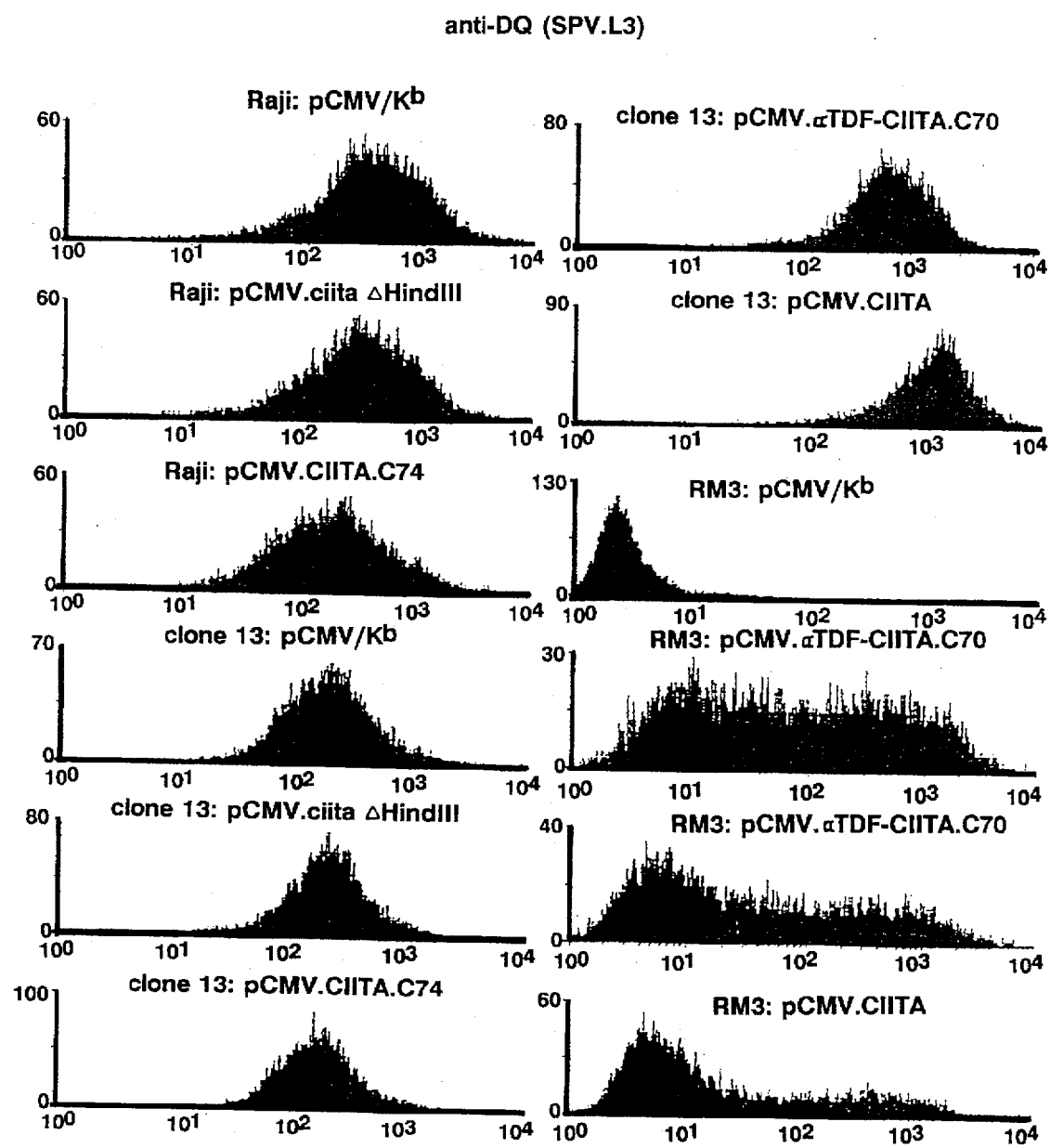
Figure 6C:
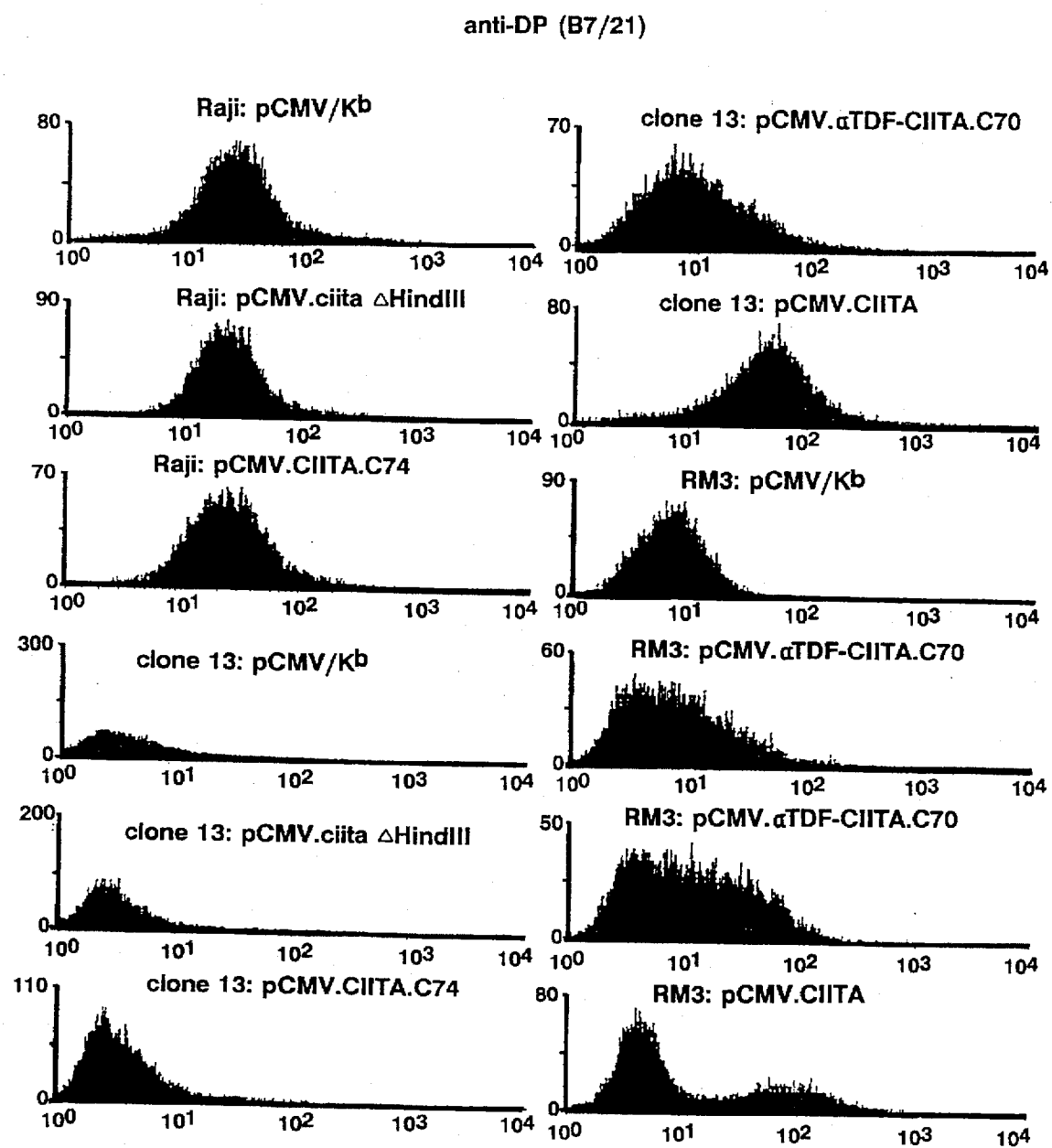
Figure 6D:
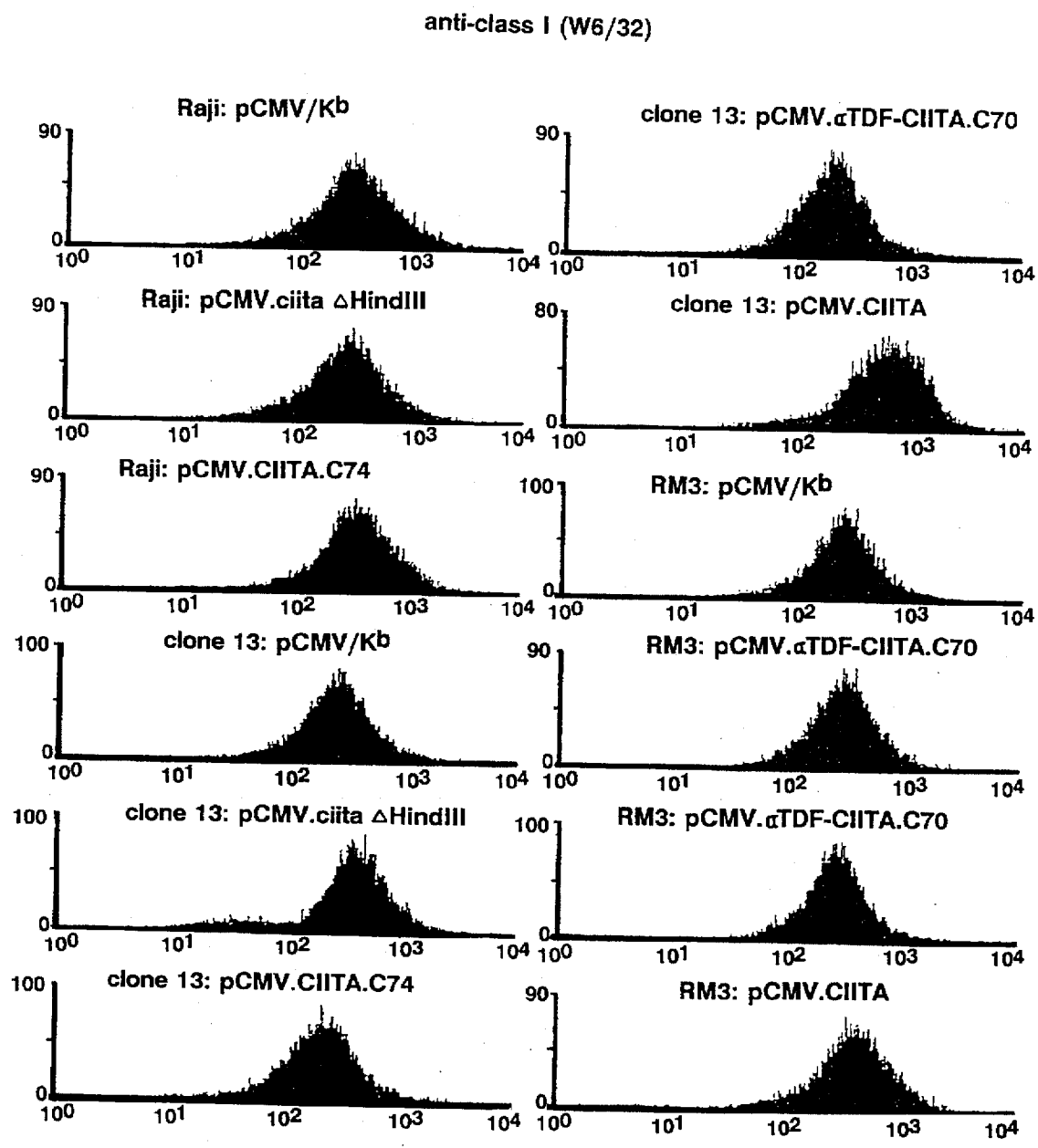
Figure 6E:
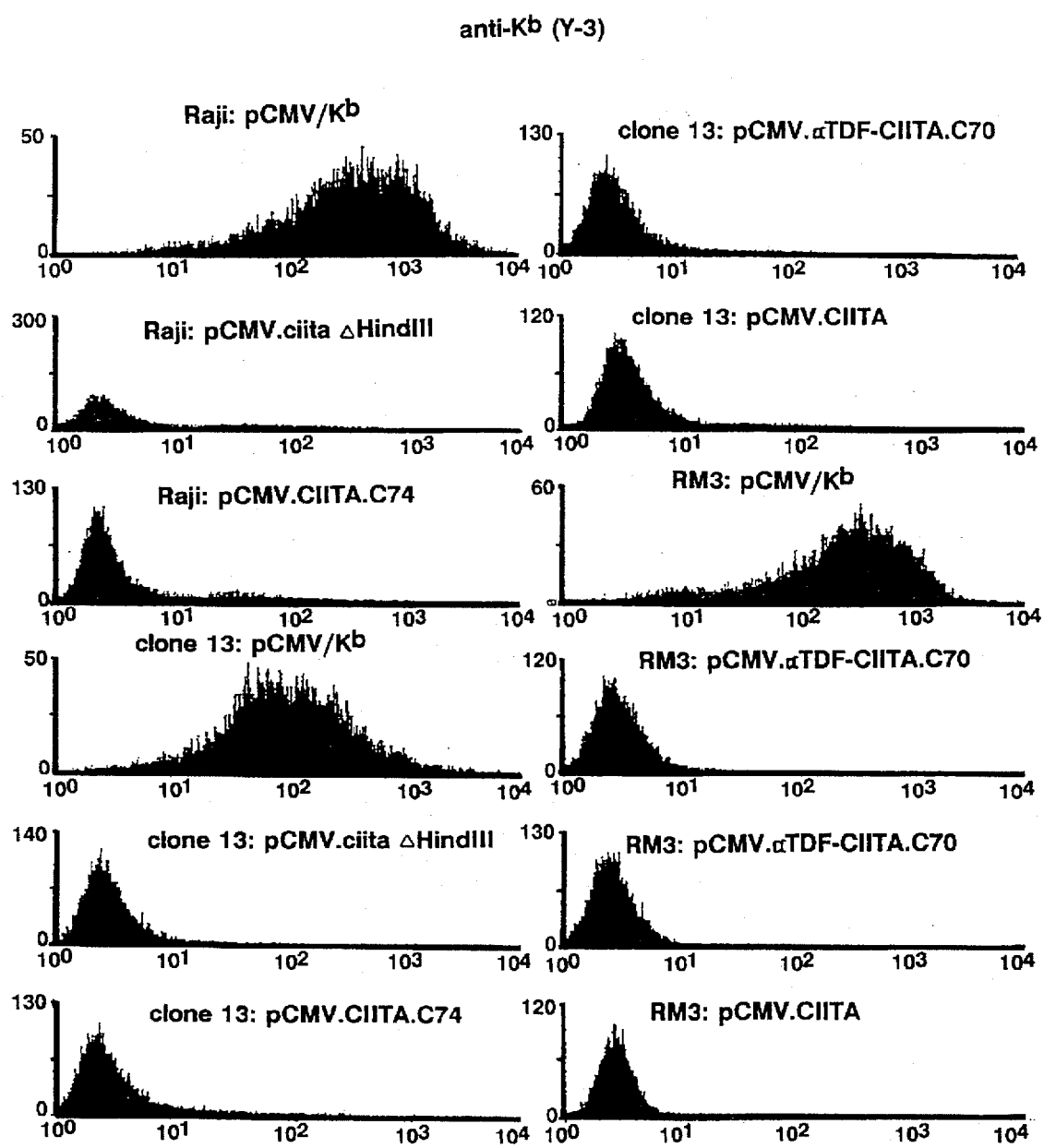

To confirm that amino acids 301–1130 encompass the CIITA interaction domain, we assayed the ability of this region of CIITA to restore MHC class II gene expression in mutant cell lines which fail to express those genes. In these studies, we used the plasmid pCMV.ciita (FIG. 5) to construct a plasmid, pCMV.αTDF-CIITA.C70 which creates a fusion protein between the interaction domain of CIITA and the transcription activation domain of α-transducing factor of Herpes Simplex Virus (HSV) strain F. As a negative control, a plasmid, pCMV.CIITA.C74, was created in which the CIITA transcription activation domain was deleted. For a second negative control, pCMV.ciitaΔHindIII, which encodes the CIITA transcription activation domain in the absence of an interaction domain, was used. As a control for transfection efficiency, cell were transfected with pCMV/$K^b$. As a positive control, the cells were transfected with pCMV.ciita which encodes the full-length CIITA. These plasmids were transfected, independently, into human B cells. One B cell line, RM3, is deficient in expression of the DR, DP, and DQ isotypes. A second B cell line, clone 13, is deficient in expression of DR and DP, but not DQ. The third cell line, Raji, expresses wild-type levels of the three MHC class II genes. Cells from each line were stained, using standard techniques, with antibodies against DR (LB3.1), DQ (SPY.L3, which are equivalent to Genox.53), DP (B7/21), class I molecules (W6/32) or $K^b$ (Y-3) and then analyzed by fluorescence activated cell sorting (FACS; FIG. 6). These data indicate that expression of the α-TDF/CIITA interaction domain fusion protein in mammalian B cells restores expression of the MHC class II genes on the surface of the mutant cell lines. Thus, amino acids 301–1130 of CIITA can function as an interaction domain.

EXAMPLE 2

Cell-based Assay of Compounds Which Are Interaction Domain Inhibitors

The above-described method can be modified to provide a method of determining whether a compound inhibits CIITA-dependent transcription. In this method, a compound to be tested is simply added to the culture of transfected cells. A compound which inhibits the ability of the α-TDF/CIITA fusion protein to restore expression of the MHC class II molecules on the cell surface is a potential autoimmune disease therapeutic. This method also permits the identification of compounds which are isotype-specific inhibitors of transcription. For example, a compound which causes the α-TDF/CIITA fusion protein to restore expression of only a subset of the MHC class II genes is an isotype-specific inhibitor. Such a compound is particularly valuable as a potential autoimmune disease therapeutic because it allows for selective inhibition of MHC class II gene transcription. The cell-based assay described above can be used alone or in conjunction with the assay described below which employs two fusion proteins.

The CIITA-Interacting Target Protein

In other assays, a compound which inhibits CIITA-dependent transcription can also be identified by virtue of its ability to inhibit binding of the CIITA interaction domain to its target protein in the cellular transcription machinery. Now that we have discovered that the function of amino acids 301–1130 of CIITA is to mediate transcription by binding to another protein(s) (referred to herein as the target protein(s)) in the cell, the CIITA target protein can be cloned rapidly and conveniently by employing the widely-used technique known as interaction trap cloning. As described below, a modification of interaction trap cloning can be used to identify compounds which inhibit binding of the CIITA interaction domain to its target protein; such compounds are potential autoimmune disease therapeutics. Briefly, interaction trap cloning employs the interaction domain of a protein and the activation domain of a second protein to rapidly and easily identify a target protein with which the interaction domain associates. The target protein enables the interaction domain to mediate transcription of a reporter gene; transcription can be assayed as described infra. Using this system, and the CIITA interaction domain which we have discovered, the target protein of the CIITA interaction domain can be cloned rapidly and easily. There now follows a description of cloning the CIITA target protein and the use of the CIITA interaction domain to identify potential autoimmune disease therapeutics.

EXAMPLE 3

Cloning the CIITA-Interacting Target Protein

To clone the target protein of the CIITA interaction domain, a host cell (e.g., a yeast cell of the strain EGY48) is transformed with a first plasmid which encodes a first fusion protein. The first fusion protein includes a DNA binding region (e.g., the N-terminal 202 amino acids of LexA) fused to the CIITA interaction domain without a CIITA activation domain. The yeast cell also carries a reporter gene (e.g., a lacZ, CAT, GUS, human growth hormone, alkaline phosphatase, or luciferase gene) which is operably linked to a regulatory sequence to which the first fusion protein binds. The reporter gene can be located on a plasmid or a chromosome. In addition, the yeast cell is transformed with a plasmid which encodes a second fusion protein. The second fusion protein includes the transcription activation domain of a protein (e.g., the B42 acidic activation domain (Ma et al., 1988, Cell 55:443–446)) fused to a test polypeptide which is assayed for its ability to mediate transcription of the reporter gene as described infra. The polypeptide which permits transcription of the reporter gene is the target protein of the CIITA interaction domain. DNA molecules encoding the potential target protein are obtained from a library (such as a cDNA library prepared from poly-$A^+$ RNA obtained from the human Burkitt's B cell lymphoma, Raji). In control assays, the CIITA interaction domain is replaced by the interaction domain of another protein (e.g., pHRFM1 or CDK2 (Zervos and Gyuris, infra)).

EXAMPLE 4

Use of the CIITA Interaction Domain to Identify Autoimmune Disease Therapeutics

Compounds which inhibit transcription by interfering with the CIITA interaction domain can be identified by assaying the compound's ability to inhibit binding of the CIITA interaction domain to its target protein. Any method which measures protein-protein interactions can be used to identify compounds which, when added to the assay, inhibit the protein-protein interaction. For example, assays based on ELISAs, Southwestern blotting, filter- and membrane-bound proteins, and immobilized proteins are among the assays which can be used to measure inhibition of binding of the CIITA interaction domain to its target protein. There now follows a detailed example of a method for identifying compounds which inhibit the function of the CIITA interaction domain, and which, therefore, are potential autoimmune disease therapeutics.

In one preferred method, a host cell (e.g., a yeast cell of the strain EGY48) is transformed with a first plasmid which encodes a first fusion protein. The first fusion protein includes a DNA-binding protein (e.g., the N-terminal 202 amino acids of LexA) fused to the CIITA interaction domain without a CIITA activation domain. The yeast cell also carries a reporter gene (e.g., a lacZ, CAT, GUS, human growth hormone, alkaline phosphatase, or luciferase gene) which is operably linked to a regulatory sequence to which the fusion protein binds. The reporter gene can be located on a plasmid or a chromosome. In addition, the yeast cell is transformed with a plasmid which encodes a second fusion protein. The second fusion protein includes the transcription activation domain of a protein (e.g., B42) fused to the target protein of the CIITA interaction domain.

Useful compounds are identified by their ability to inhibit transcription of the reporter gene in this assay. Small cultures of the transformed cells are mixed with the compounds to be tested and grown in a medium which is suitable to maintain expression of the plasmids, and under suitable conditions (e.g., at 30° C. with agitation overnight). The level of gene expression is then measured. For example, if the lacZ gene is used as the reporter gene, the amount of blue chromophore produced in the presence of X-gal can be determined (e.g., by measuring the optical density or by manually examining the color of the cell cultures). Compounds which inhibit activation of transcription in assays employing the CIITA interaction domain but not the control interaction domain can inhibit expression of the MHC class II molecules, and, therefore, are strong candidates for autoimmune disease therapeutics. This assay can be used alone or in combination with the cell-based assay described in Example 2.

Identification of The CIITA Clone 13 Mutant

We have identified a mutation in CIITA which alters the protein's ability to activate transcription of certain MHC class II isotypes. This mutant CIITA, termed clone 13 CIITA, is present in the clone 13 cell line, a derivative of the human B cell lymphoma, Jijoye (available from L. Glimcher, Harvard University, Mass.). The clone 13 CIITA is defective in transcription of the DR and DP isotypes but not the DQ isotype of the MHC class II genes. We have discovered that expression of the wild-type CIITA gene in clone 13 cells enables the cells to transcribe the DR and DP isotypes. In these studies, the CIITA gene was cloned into the vector pCMV, and the resulting vector, pCMV.ciita (FIG. 5), was then transfected by electroporation into clone 13 cells.

The transfected cells were analyzed by FACS for expression of the DR and DP isotypes (FIG. 7). As controls, Raji cells (which express the DR, DP, and DQ isotypes) and the untransformed clone 13 cells were examined in the same manner. Standard techniques were used to stain the cells with antibodies. In addition to staining the cells with anti-DR (LB3.1; L243 antibodies from Becton-Dickinson can also be used), anti-DQ (Genox.53; ATCC #HB103), or anti-DP (B7/21; Becton-Dickinson) antibodies, the cells were stained with anti-class I antibodies (W6/32; a positive control, ATCC #HB95) and anti-Kb antibodies (Y-3; a negative control, ATCC #HB176). Referring to FIG. 7, expression of CIITA in clone 13 cells increases the relative fluorescence of those cells when they are stained with anti-DP, anti-DR, or anti-DQ antibodies. Thus, expression of wild-type CIITA in clone 13 cells corrects the deficiency of the clone 13 mutant CIITA.

EXAMPLE 5

Identification of Isotype-Specific Compounds

The interaction domain of the clone 13 mutant CIITA can be used in the assays described in Example 4 to identify compounds which are isotype-specific inhibitors of CIITA-dependent transcription. If desired, the clone 13 CIITA transcription activation domain or full-length polypeptide can be used in other assays to identify useful compounds. Compounds which inhibit CIITA-dependent transcription involving wild-type CIITA, but not the clone 13 mutant CIITA, are useful for inhibiting expression of the DR and DP MHC class II isotypes without inhibiting expression of the DQ isotype. Such compounds are isotype-specific and can be used to inhibit the expression of particular genes involved in the induction of an immune response, without causing generalized immunosuppression. Because numerous autoimmune diseases, such as rheumatoid arthritis (see Tables 1 and 2) are associated with particular isotypes, compounds which can inhibit expression of a subset of the MHC class II genes are particularly valuable for selectively affecting the immune system.

Other Embodiments

Other embodiments are within the following claims. For example, the activation and interaction domains of isotype-specific CIITA mutants other than the clone 13 CIITA are within the invention. Isotype-specific CIITA mutants can be identified as described above for the clone 13 CIITA. Cell lines which are defective in expression of a subset of the MHC class II genes are candidate sources of isotype-specific CIITA proteins. A cell line containing an isotype-specific CIITA can be identified by expressing wild-type CIITA in the candidate cell line and determining whether expression of CIITA corrects the deficiency in expression of the MHC class II gene(s). The mutant CIITA gene can be cloned using the techniques described for the clone 13 CIITA. Thus, the methods presented in Example 5 are useful for isolating other isotype-specific CIITA mutants which can be used to determine whether a compound is an isotype-specific inhibitors of transcription.

Additional methods of assaying CIITA-dependent transcription also are within the invention. For example, previously-described transcription assays (see, e.g., Keegan et al., 1986, Science 23: 699; Ma et al., 1987, Cell 48: 847; Lin et al., 1988, Cell 54: 659; Sadowski et al., 1988, Nature 335: 563; Roberts et al., 1993, Nature 363: 741; and Ma et al., 1988, Cell 55: 443) can, with appropriate substitution of the CIITA transcription activation domain, be used for identifying useful compounds, by simply adding the compounds to the assay. In addition, modifications of the above-described assay can be used in the invention. For example, other DNA-binding proteins, such as GAL4, can be used in place of LexA. Reporter genes, such as chloramphenicol acetyl transferase (CAT), luciferase, $\beta$-glucuronidase (GUS), human growth hormone, alkaline phosphatase or any gene whose expression can be assayed can substitute for the lacZ gene. Host cells other than yeast also can be used; for example, prokaryotic and other eukaryotic cells (e.g., bacterial, mammalian and plant cells) are useful. Methods of measuring protein-protein interactions, such as assays based on ELISAs, Southwestern blotting, filter- and membrane-bound proteins, and immobilized proteins also can be used to identify compounds which inhibit binding of the CIITA interaction domain to its target protein. It will be readily apparent that standard techniques of molecular biology will enable one to use the CIITA interaction domain in other assays of protein-protein interactions.

Construction of Plasmids

The original CIITA templates were obtained by RT-PCR with polyA$^+$ RNA extracted from the HLA class II positive B lymphoid cell line Raji. The PCR products were then directly cloned into pCRII (Invitrogen). Of the clones obtained, three (pCRII.ciita.b, pCRII.ciita.h, and pCRII.ciita.p) were used to generate a complete cDNA eukaryotic expression construct (See FIGS. 5 and 8).

pCRII.ciita.b: The CIITA-specific PCR primers used for this construct were 5'-GGAAGCTGAGGGCACGAGGAG-3' for the 5' end and 3'-CAGAAGAGACAGGGGACGGTAAC-5' for the 3' end.

pCRII.ciita.h: The CIITA-specific PCR primers used for this construct were 5'-CTCCAACAAGCTTCCAAAATG-3' for the 5' end and 3'-GTACAAGAGACTCCTGTGATTG-5' for the 3' end.

pCRII.ciita.p: The CIITA-specific PCR primers used for this construct were 5'-GTCCCTGAAGGATGTGGAAGAC-3' for the 5' end and 3'-GTCTGACCTTCGTGTCGAAG-5' for the 3' end.

pCMV.ciita: This construct was made via multistep sub-cloning using pLB-1 as the vector and pCRII.ciita.b, pCRI-I.ciita.h and pCRII.ciita.p as inserts. First, the vector DNA was prepared by cutting pLB-1 with HindIII, treating with T4 polymerase, followed by NotI activation digestion; the 5' CIITA DNA insert was prepared by cutting pCRII.ciita.b with EcoRI at sites which flank the PCR insert in pCRII constructs, gel purification of the smaller fragment, T4 polymerase treatment, followed by NotI activation digestion (NotI at nucleotide 1340 in the CIITA sequence). These two fragments were ligated with T4 ligase and the resulting pCMV.ciita sub-construct is termed pCMV.ciita.b.

pCMV.ciita.b was then digested with BamHI, and the smaller fragment was gel-purified, blunted T4 polymerase, and activated by NotI digestion; pCRII.ciita.p was similarly cut with EcoRI, blunted with T4 polymerase, and followed by NotI activation digestion. The smaller fragment was gel-purified and used. The vector and insert fragments were ligated with T4 ligase, and the resulting pCMV.ciita second sub-construct was termed pCMV.ciita.bp.

pCMV.ciita.bp was further digested with BamHI and NotI; pCRII.ciita.h was also cut with BamHI and NotI, and the smaller fragment was gel-purified. These two fragments were ligated with T4 ligase and the resulting construct which contains CIITA cDNA sequences (nucleotides 48–4471) is termed pCMV.ciita.bp.

pCMV.CIITA: This construct was made after pCMV.ciita had been constructed and confirmation of its biological function in restoring HLA class II general expression (by transfection of HLA class II-negative cell lines (RM3 and clone 13) and FACS analysis). The CIITA cDNA construct termed pKS/CIITA (+) (from Dr. B. Mach, University of Geneva; Geneva, Switzerland) was also used in these experiments. In this plasmid, the vector was pBluescript KS(+) (Stratagene), and the cDNA was inserted into the SalI site of the multiple cloning site. To make pCMV.CIITA, pCMV was digested with XhoI and NheI, and the CIITA cDNA fragment was obtained by cutting pKS/CIITA with XhoI and SpeI whose recognition sites flank the cDNA insert. The two fragments were ligated with T4 ligase, and the resulting construct was termed pCMV.CIITA (the upper-case letters indicate that the DNA source was from original cDNA library).

pEG.CIITA: This plasmid was made using pEG.CII-TA.SalI and pTrc.CIITA. pEG.CIITA.SalI was digested with BamHI and the larger fragment was gel-purified; the CIITA sequence was obtained by digesting pTrc.ciita with BamHI, and the vector and insert were ligated with T4 ligase.

pEG.CIITA.SalI pEG202 was first linearized with SalI and dephosphorylated with CIP; CIITA cDNA was obtained by SalI digestion of pCMV.CIITA; the vector and insert fragment were then ligated and the resulting intermediate pEG construct with the CIITA cDNA insert was termed pEG.CIITA.SalI.

pTra.ciita This construct was originally generated from over-expression of the recombinant CIITA protein. First the 5' CIITA sequence was cloned (using PCR, in the same way as in the construction of pEG.ciita. N29, below) into the BamHI site and the XhoI site of pTrcHis C (Invitrogen). The resulting plasmid, termed pTrc5 or pTrc/ciita5, was linearized with XhoI, blunted with T4 polymerase, and activated with DraIII; the downstream 3790 bp of CIITA was obtained by digesting pCMV.ciita with ScaI and DraIII, and the two fragments were ligated.

pEG.ciita.N29: A pair of PCR primers was designed in order to fuse the N-terminal 29% of CIITA in-frame into pEG202, following the 202nd codon of the LexA N-terminus. The sequence for the 5' back primer is AATG-GATCcgttgcctggctcca (upper case letters indicating the tagged sequence which includes a BamHI site for in-frame cloning) and the sequence of the 3' forward primer is CCGCTCGAGcggcaccatacgtgt (the tagged sequence includes an XhoI site). These primers were used with the full length CIITA cDNA template in polymerase chain reaction (PCR) to generate a 1060 bp fragment. The PCR reaction profiles were 3 cycles of 95° C. for 5 minutes, 55° C. for 5 minutes, and 72° C. for 3 minutes; followed by 30 cycles of 95° C. for 1 minute, 60° C. for 2 minutes, and 72° C. for 1 minute. The resulting DNA fragment was digested with BamHI and XhoI, and cloned into the corresponding BamHI and XhoI sites of the pEG202 vector. The stop codon for this fusion protein is provided by the vector sequence following the XhoI site of pEG202.

pCMV and pLB-1: pCMV is an EBV over-expression vector generated by partial digestion of pREP7 (Invitrogen) with SalI; insertion of a BglII linker into the second SalI site (nt.1091) after blunting it with Klenow; double digestion with HindIII and BglII; and finally ligation with the CMV promoter fragment from pCDM8 (Invitrogen), which was prepared by SpeI digestion of pCDM8; blunting with Klenow; BglII linker insertion; and HindIII and BglII digestion and gel-purification. The actual vector used to make the first ciita (lower-case letters indicate the construct was a PCR-derived product) subconstruct was pLB-1, which was derived from pCMV by inserting a ~1 kb stuffer DNA between the HindIII and NotI sites to facilitate HindIII/NotI double digestion.

pEG.CIITA.C74: pEG202 was linearized with BamHI, blunted with T4 polymerase and activated with SalI; the insert was prepared by digesting pCMV.CIITA with SphI, blunting with T4 polymerase, and activating with SalI; the two fragments were then ligated.

pEG.CIITA.C50: pEG202 was linearized with EcoRI, blunted with T4 polymerase and activated with SalI; the insert was prepared by digesting pCMV.CIITA with NcoI, blunting with T4 polymerase, and activating with SalI; the two fragments were then ligated.

pEG.CIITA.C30: pEG202 was linearized with BamHI, blunted with T4 polymerase, and activated with SalI; the insert was prepared by digesting pCMV.CIITA with KpnI, blunting with T4 polymerase, and activating with SalI; the two fragments were then ligated.

pEG.CIITA.C14: pEG.CiiTA was completely cut with BamHI, diluted, and ligated. A recircularized deletion construct which contains the CIITA ORF N-14% was isolated using standard techniques.

pEG.ciita.N70: pEG202 was linearized with XhoI, blunted with T4 polymerase, and activated with BamHI. The insert was prepared by digesting pET.ciiTA with KpnI, blunting with T4 polymerase, and activating with BamHI; the two fragments were then ligated. pET.ciiTA, a construct for over-expression of CIITA, was made by cloning the CIITA open reading frame, as in the construction of pEG.ciiTA (above), into pET28c (Novagen).

pEG.ciita.N56: pEG202 was libearized with XhoI, blunted with T4 polymerase and activated with BamHI; the insert was prepared by digesting pET.ciiTA with SfiI, blunting with T4 polymerase, and activating with BamHI; the two fragments were then ligated.

pEG.ciita.N22: The insert was obtained by digesting the ciita-containing NheI/XhoI fragment of pTrc5 with BanI, blunting with T4 polymerase and cutting with BamHI. The vector was prepared by linearizing pEG202 with XhoI, blunting with T4 polymerase and finally cutting with BamHI. The prepared insert and vector then were ligated.

pEG.ciita.N17: The insert was obtained by digesting the small NheI/XhoI fragment of pTrc5 with EaeI, blunting with T4 polymerase and finally cutting with BamHI. The vector was prepared by linearizing pEG202 with XhoI, blunting with T4 polymerase and finally cutting with BamHI. The prepared insert and vector then were ligated.

pEG.ciita.N12: The insert was obtained by digesting the small NheI/XhoI fragment of pTrc5 with MspI, blunting with T4 polymerase and finally cutting with BamHI. The vector was prepared by linearizing pEG202 with SalI, blunting with T4 polymerase and finally cutting with BamHI. The prepared insert and vector then were ligated in frame.

pEG.ciita.N7.6: The insert was obtained by digesting the small NheI/XhoI fragment of pTrc5 with EcoNI, blunting with T4 polymerase and finally cutting with BamHI; the vector was prepared by linearizing pEG202 with XhoI, blunting with T4 polymerase and finally cutting with BamHI. The prepared insert and vector then were ligated.

pEG.C-αTDF: This construct was made by inserting the C-terminal 16% of HSV1 (strain F) α-transducing factor (Pellett et al., 1985, PNAS 82:5870–5874; accession number K03350) into pEG202.

pEG.C'-αTDF: This construct was made by inserting the C-terminal 16% (except the very C-terminal 3 codons,) of HSV1 (strain F) α-transducing factor. The insert in this construct was later used to construct pCMV.αTDF-CIITA.C70.

pCMV.ciita ΔHindIII: This construct contains the CIITA N-terminal 29% of the ORF, and was made by digesting pCMV.ciita with HinddIII, purifying the major band and recircularizing.

pCMV.CIITA.C74: This construct contains the N-terminal 25 codons and about 74% of the C-terminal ORF of CIITA. It was generated by multistep subloning. First, pKS/CIITA(+) was cut with NcoI, blunted with T4 polymerase and then cut with XhoI as the vector. In parallel, it was cut with SphI, blunted with T4 polymerase, and then cut with XhoI as the insert. The two fragments were ligated with T4 polymerase, and the resulting construct was termed pKS.CIITA ΔN/S. To generate pCMV. CIITA.C74, pKS.CIITA ΔN/S was cut with SpeI and XhoI, and the CIITA-containing fragment was then inserted into NheI/XhoI cut pCMV vector.

pCMV.αTDF-CIITA.C70: This was generated by multistep subcloning. First, pKS/CIITA(+) was cut with Tth111I, blunted with T4 polymerase, and then ligated with T4 ligase. This intermediate construct was termed pKS/CIITA.ΔTth. It was then cut with NcoI and AatII, blunted with T4 polymerase, and ligated in-frame with a fragment which encodes the C-terminal 16%, (except the very C-terminal 3 codons) of HSV1 (strain F) α-transducing factor. This second intermediate construct was termed pKS/αTDF-CIITA.ΔTth. The 5' αTDF-CIITA containing NotI fragment was then used to replace the corresponding 5' NotI fragment of pKS/CIITA(+). This third intermediate construct was termed pKS/αTDF-CIITAC.70. To generate pCMV.αTDF-CIITA.C70, pKS/αTDF-CIITAC.70 was cut with SpeI and XhoI. The αTDF-CIITA containing fragment was then inserted into NheI/XhoI cut pCMV vector.

---

What is claimed is:

1. A method of determining whether a compound inhibits the ability of a polypeptide to activate transcription, the polypeptide being characterized in that it comprises a CIITA transcription activation domain and lacks a functional CIITA interaction domain, wherein inhibition of transcription indicates that said compound is a potential autoimmune disease therapeutic.

2. The method of claim 1, wherein inhibition of transcription activation is measured by a) providing a fusion protein comprising said polypeptide fused to a DNA-binding protein;

b) providing a transcription regulatory DNA sequence, operably linked to a reporter gene in a system suitable for transcribing said reporter gene when said fusion protein is bound to said regulatory DNA sequence;

c) providing said fusion protein and said compound in said system; and d) measuring the ability of said compound to inhibit transcription of said reporter gene.

3. The method of claim 1, further comprising measuring the ability of said compound to inhibit the ability of a second polypeptide to activate transcription, the second polypeptide being characterized in that it comprises an isotype-specific CIITA transcription activation domain and lacks a functional CIITA interaction domain, wherein said method identifies isotype-specific compounds.

4. A substantially pure DNA encoding a CIITA isotype-specific transcription activating polypeptide including amino acids 26–352 of SEQ ID NO:1, or a variant thereof that functions as an activation domain of CIITA but not as an interaction domain of CIITA.

5. The DNA of claim 4, wherein said DNA has the sequence of nucleotides 76–1056 of SEQ ID NO:1, or encodes a polypeptide that functions as an activation and not as an interaction domain of CIITA but differs from amino acids 26–352 of SEQ ID NO:1 by one or more conservative amino acid substitutions.

6. The DNA of claim 4, wherein said DNA has the sequence of nucleotides 76–1056 of SEQ ID NO:1, or encodes the same amino acid sequence as nucleotides 76–1056 of SEQ ID NO:1.

7. A substantially pure DNA encoding a CIITA transcription activating polypeptide including amino acids 26–352 of SEQ ID NO:1, said polypeptide functioning as an activation domain but not as an interaction domain of CIITA.

8. A substantially pure polypeptide comprising a CIITA transcription activation domain and lacking a functional CIITA interaction domain.

9. The polypeptide of claim 8 comprising an amino acid sequence including amino acids 26–352 of SEQ ID NO:1 or a variant thereof that functions as an activation domain, but not as an interaction domain, of CIITA.

10. The polypeptide of claim 8 wherein said CIITA is isotype-specific.

11. The polypeptide of claim 8, wherein said polypeptide has the sequence of amino acids 26–352 of SEQ ID NO:1, or a polypeptide that functions as an activation and not as an interaction domain of CIITA but differs from amino acids 26–352 of SEQ ID NO:1 by one or more conservative amino acid substitutions.

12. A method of determining whether a compound inhibits the ability of a polypeptide to bind its target protein, said polypeptide being characterized in that it comprises a CIITA interaction domain and lacks a functional CIITA activation domain, wherein inhibition of binding indicates that said compound is a potential autoimmune disease therapeutic.

13. The method of claim 12, said method comprising determining whether said compound inhibits the ability of said polypeptide to mediate transcription, inhibition of transcription indicating that said compound is a potential autoimmune disease therapeutic.

14. The method of claim 13, wherein said inhibition is measured by
   a) providing a first fusion protein comprising said polypeptide fused to a DNA binding protein;
   b) providing a reporter construct comprising DNA regulatory sequence for said DNA binding protein, operably linked to a reporter gene in a system suitable for transcribing said reporter gene;
   c) providing a second fusion protein, said second fusion protein being characterized in that it comprises a transcription activation domain fused to the target protein of a CIITA interaction domain;
   d) providing said first and second fusion proteins, said reporter construct, and said compound in a transcription system; and
   e) measuring the ability of said compound to inhibit transcription of said reporter gene.

15. The method of claim 12, further comprising measuring the ability of said compound to inhibit the ability of a second polypeptide to bind its target protein, said second polypeptide being characterized in that it comprises an isotype-specific CIITA interaction domain and lacks a functional CIITA transcription activation domain, wherein said method identifies isotype-specific compounds.

16. A substantially pure DNA encoding a CIITA polypeptide including amino acids 301–1139 of SEQ ID NO:1, or a variant thereof that functions as an interaction domain of CIITA, but not as an activation domain of CIITA.

17. The DNA of claim 16, wherein said DNA has the sequence of nucleotides 903–3390 of SEQ ID NO:1, or encodes a polypeptide that functions as an interaction and not as an activation domain of CIITA but differs from amino acids 301–1130 of SEQ ID NO:1 by one or more conservative amino acid-substitutions.

18. The DNA of claim 16, wherein said DNA encodes a polypeptide comprising amino acids 301–1130 of SEQ ID NO:1.

19. The DNA of claim 16, wherein said CIITA is isotype-specific.

20. A substantially pure polypeptide comprising a CIITA interaction domain and lacking a functional CIITA transcription activation domain.

21. The polypeptide of claim 20, wherein said polypeptide has the sequence of amino acids 301–1130 of SEQ ID NO:1, or a polypeptide that functions as an interaction and not as an activation domain of CIITA but differs from amino acids 301–1130 of SEQ ID NO:1 by one or more conservative amino acid substitutions.

22. The polypeptide of claim 20, including amino acids 301–1130 of SEQ ID NO:1, or a variant thereof that functions as an interaction domain, but not as an activation domain, of CIITA.

23. The polypeptide of claim 20, wherein said CIITA is isotype specific.

24. A method of determining whether a compound inhibits the ability of a polypeptide to mediate transcription, said polypeptide being characterized in that it comprises a CIITA interaction domain fused to a transcription activation domain and lacks a functional CIITA transcription activation domain, wherein inhibition of transcription indicates that said compound is a potential autoimmune disease therapeutic.

25. The method of claim 24, further comprising providing said polypeptide in a B lymphocyte and assaying for expression of the MHC class II genes.

* * * * *

UNITED STATES PATENT AND TRADEMARK OFFICE
CERTIFICATE OF CORRECTION

PATENT NO. : 5,672,473
DATED : September 30, 1997
INVENTOR(S) : Laurie H. Glimcher, Hong Zhou and John Douhan It is certified that error appears in the above-indentified patent and that said Letters Patent is hereby corrected as shown below:

Column 27, line 34,

In claim 16, "1139" should read "1130".

Signed and Sealed this

Twenty-fourth Day of February, 1998

*Attest:*

BRUCE LEHMAN

*Attesting Officer*          *Commissioner of Patents and Trademarks*